US010676757B2

(12) United States Patent
Hey et al.

(10) Patent No.: US 10,676,757 B2
(45) Date of Patent: Jun. 9, 2020

(54) IRDIG17912 INSECTICIDAL CRY TOXINS

(71) Applicant: Dow AgroSciences LLC, Indianapolis, IN (US)

(72) Inventors: Timothy D. Hey, Zionsville, IN (US); Janna Mai Armstrong, Indianapolis, IN (US); Ted Letherer, Indianapolis, IN (US); Audrey Jane Etter, Indianapolis, IN (US); Meghan L. Frey, Greenwood, IN (US); Haley Ellis, Indianapolis, IN (US); Kenneth E. Narva, Zionsville, IN (US); Xiaoping Xu, Yinchuan (CN); Krishna M. Madduri, Indianapolis, IN (US); Sek Yee Tan, Carmel, IN (US); Premchand Gandra, Zionsville, IN (US)

(73) Assignee: DOW AGROSCIENCES LLC, Indianapolis, IN (US)

( * ) Notice: Subject to any disclaimer, the term of this patent is extended or adjusted under 35 U.S.C. 154(b) by 147 days.

(21) Appl. No.: 15/237,918

(22) Filed: Aug. 16, 2016

(65) Prior Publication Data
US 2017/0058293 A1    Mar. 2, 2017

Related U.S. Application Data

(60) Provisional application No. 62/209,586, filed on Aug. 25, 2015.

(51) Int. Cl.
*C07K 14/325* (2006.01)
*C12N 15/82* (2006.01)

(52) U.S. Cl.
CPC ........ *C12N 15/8286* (2013.01); *C07K 14/325* (2013.01); *Y02A 40/162* (2018.01)

(58) Field of Classification Search
None
See application file for complete search history.

(56) References Cited

U.S. PATENT DOCUMENTS

2013/0097729 A1* 4/2013 Bonning .............. C07K 14/325
                                                    800/279
2013/0205440 A1* 8/2013 Lira .................... C12N 9/1092
                                                    800/278
2016/0311864 A1* 10/2016 Parks .................... A01N 37/46

FOREIGN PATENT DOCUMENTS

| WO | WO1995002693 A1 | 1/1995 |
| WO | 2007/027776 A2 | 3/2007 |
| WO | 2013/134734 A2 | 9/2013 |
| WO | 2014/138339 A2 | 9/2014 |

OTHER PUBLICATIONS

Loth et al (New Cyt-like d-endotoxins from Dickeya dadantii: structure and aphicidal activity. Scientific Reports. 10.1038, p. 1-10, Mar. 2015).*
Gagat et al (How protein targeting to primary plastids via the endomembrane system could have evolved? A new hypothesis based on phylogenetic studies. Biology Direct. 8:18, p. 1-22, 2013).*
Crickmore, N. et al., Revision of the Nomenclature for the Bacillus thuringiensis Pesticidal Crystal Proteins, Microbiology and Molecular Biology Review, 1998, 807-813, vol. 62, No. 3, American Society for Microbiology, US.
Guerchicoff, Alejandra, et al., Identification an Characterization of a Previously Undescribed cyt Gene in *Bacillus thuringiensis* subsp. *israelensis*, Applied and Environmental Microbiology, 1997, p. 2716-2721, vol. 63, No. 7, American Society for Microbiology, US.
Koni, P.A., et al., Cloning and Characterization of a Novel Bacillus thuringiensis Cytolytic Delta-Endotoxin, 1993, Journal of Molecular Biology, V. 229, p. 319-327, Elsevier.
Guerchicoff, Alejandra; et al.: "The Bacillus thuringiensis cyt Genes for Hemolytic Endotoxins Constitute a Gene Family", Applied and Environmental Microbiology, Mar. 1, 2001 (Mar. 1, 2001), vol. 67, No. 3, pp. 1090-1096.
Soberon, Mario; et al.: "Cyt toxins produced by Bacillus thuringiensis: A protein fold conserved in several pathogenic microorganisms", Peptides, Jun. 9, 2012 (Jun. 9, 2012), vol. 41, pp. 87-93.
International Search Report, International Preliminary Report on Patentability, and Written Opinion for International Application No. PCT/US2016/047131, dated Nov. 3, 2016.

* cited by examiner

*Primary Examiner* — Medina A Ibrahim
*Assistant Examiner* — Wayne Zhong

(57) ABSTRACT

Insecticidal toxins derived from *Bacillus thuringiensis*, polynucleotides encoding such toxins, use of such toxins to control plant pests, and transgenic plants that produce, and are protected, by these toxins are described.

11 Claims, No Drawings

Specification includes a Sequence Listing.

IRDIG17912 INSECTICIDAL CRY TOXINS

CROSS-REFERENCE TO RELATED APPLICATIONS

This application claims priority from, and benefit of, U.S. Provisional Application 62/209,586 filed on Aug. 25, 2015. The entire contents of this application is hereby incorporated by reference into this application.

REFERENCE TO SEQUENCE LISTING SUBMITTED ELECTRONICALLY

The official copy of the sequence listing is submitted electronically via EFS-Web as an ASCII formatted sequence listing with a file named "76327-US-PSP 20150825_Sequence_Listing_FINAL_ST25", created on Aug. 4, 2016, and having a size of 35 kilobytes, and is filed concurrently with the specification. The sequence listing contained in this ASCII formatted document is part of the specification, and is incorporated herein by reference in its entirety.

TECHNICAL FIELD

The present invention relates generally to the field of molecular biology as applied to agricultural sciences. More particularly, certain embodiments concern methods and such as, for example, the use of DNA segments as diagnostic probes and templates for protein production, and the use of proteins, fusion protein carriers and peptides for insect control and in various immunological and diagnostic applications. Also disclosed are methods of making and using nucleic acid segments in the development of transgenic plant cells containing the DNA segments disclosed herein.

BACKGROUND

*Bacillus thuringiensis* is a Gram-positive bacterium that produces delta-endotoxins known as crystal proteins which are specifically toxic to certain orders and species of insects. Many different strains of *B. thuringiensis* have been shown to produce insecticidal crystal proteins. Compositions including *B. thuringiensis* strains which produce insecticidal proteins have been commercially available and used as environmentally acceptable insecticides.

As noted by Hofte et al., (1989) the majority of insecticidal *B. thuringiensis* strains are active against insect of the order Lepidoptera, i.e., caterpillar insects. Other *B. thuringiensis* strains are insecticidally active against insects of the order Diptera, i.e., flies and mosquitoes, or against both lepidopteran and dipteran insects. In recent years, a few *B. thuringiensis* strains have been reported as producing crystal proteins that are toxic to insects of the order coleoptera, i.e., beetles.

The dipteran-active Cyt toxins differ from most of the other *B. thuringiensis* insecticidal crystal proteins in that they are smaller and do not share conserved blocks of sequence homology. These proteins demonstrate broad cytolytic activity in vitro, yet are specifically toxic to larvae of dipteran insects in vivo. These properties have been described elsewhere (Chilcott and Ellar, 1988).

A number of genes encoding cytotoxic proteins have been cloned from several strains of *B. thuringiensis*. The review by Hate et al. (1989) discusses the genes and proteins that were identified in *B. thuringiensis* prior to 1990, and sets forth the nomenclature and classification scheme which has traditionally been applied to *B. thuringiensis* genes and proteins. cryI genes encode lepidopteran-toxic CryI proteins. cryII genes encode CryII proteins that are toxic to both lepidopterans and dipterans. cryIII genes encode coleopteran-toxic CryIII proteins, while cryIV genes encode dipteran-toxic CryIV proteins. A new nomenclature has been employed that systematically classifies the cry genes based upon DNA sequence homology rather than upon insect specificities (Crickmore, N. et al. Microbiol. and Mol. Bio. Rev. (1998) Vol. 62: 807-813; http://www.btnomenclature.info/).

The cloning and expression of a gene encoding a 26-kDa mosquitocidal toxin from the dipteran-active *B. thuringiensis* var. *israelensis* has been described (Ward et al., 1984), and the nucleotide sequence of this gene was reported (Ward and Ellar, 1986). The molecular mass of the toxin protein, CytA, calculated from the deduced amino acid sequence was determined to be 27,340 Da. The nucleotide sequence of the gene for a 27-kDa mosquitocidal Cyt protein isolated from *B. thuringiensis* var. *morrisoni* strain PG14 has been disclosed (Earp and Ellar, 1987). The sequence of this toxin protein was found to differ by only one amino acid residue from the CytIA protein of *B. thuringiensis* var. *israelensis*.

The identification of a 25-kDa protein that exhibits cytolytic activity in vitro when activated by proteolysis from the mosquitocidal *B. thuringiensis* var. *kyushuensis* was described earlier (Knowles et al., 1992), and the nucleotide sequence of the gene for this protein, CytB, was reported (Koni and Ellar, 1993). The predicted molecular mass of the CytB protein is 29,236 Da and the deduced amino acid sequence is quite distinct, although it does share significant sequence similarity with the CytA protein of *B. thuringiensis* var. *israelensis*.

The cloning and characterization of the gene for a 30-kDa toxin protein with activity on coleopteran and dipteran insects has been described (Intl. Pat. Appl. Pub. No. WO 95/02693, 1995). This gene, isolated from *B. thuringiensis* PS201T6, encodes a protein of 29,906 Da which exhibits a 64% sequence identity with the CytA toxin of *B. thuringiensis* var. *israelensis*. IRDIG17912 and the gene encoding it have little homology to the delta-endotoxins and genes of the prior art. IRDIG17912, which is a Cyt2-like toxin, demonstrates surprising insecticidal activity against insects of the order Coleoptera and Lepidoptera.

Despite the discovery of many selective protein toxins from *B. thuringiensis*, there remains a critical need to discover new, effective pest control agents that provide economic benefits to farmers, are capable of delaying or preventing the development of resistant insects, and are environmentally acceptable. Particularly needed are agents targeted to control a wide spectrum of economically important insect pests that effectively control insect populations that are, or could become, resistant to existing insect control agents and those with equal to or increased potency compared to currently deployed insecticidal protein toxins.

SUMMARY OF THE INVENTION

The present invention is based on the discovery of a novel Cyt2-like protein toxin, designated IRDIG17912, having insecticidal activity against *Diabrotica virgifera virgifera* (Western Corn Rootworm (WCR)) and *Plutella xylostella* (Diamondback Moth (DBM)). Based on the amino acid sequence of native IRDIG17912 toxin, it is classified as belonging to the Cyt2 family.

The present invention provides a novel *B. thuringiensis* insecticidal protein toxin designated IRDIG17912 and the gene encoding it designated irdig17912. The invention also includes N-terminal deletions, derivatives, analogs, and mutant forms of IRDIG17912, plant codon optimized nucleic acid sequences encoding the claimed toxins, methods for making, using the toxins and antibodies that selectively bind these toxins.

The present invention also concerns DNA segments, which can be isolated from virtually any source, that are free from total genomic DNA and that encode the whole or a portion of the novel peptides disclosed herein. The IRDIG17912 encoding gene (SEQ ID NO:1; encodes the 36.68-kDa IRDIG17912 protein having an amino acid sequence shown in (SEQ ID NO:2). DNA segments encoding these peptide species may prove to encode proteins, polypeptides, subunits, functional domains, and the like of crystal protein-related or other non-related gene products. In addition these DNA segments may be synthesized entirely in vitro using methods that are well known to those of skill in the art.

In particular embodiments, the invention concerns isolated DNA segments and recombinant vectors incorporating DNA sequences that encode the claimed toxins. More preferably, the DNA segments comprise a nucleic acid sequence that encodes a protein or peptide species that includes within its amino acid sequence an at least ten amino acid contiguous sequence of SEQ ID NO:2.

Similarly, a DNA segment comprising an isolated or purified protein-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes not only genomic sequences, including extrachromosomal DNA sequences, but also operon sequences and/or engineered gene segments that express, or may be adapted to express, proteins, polypeptides or peptides.

BRIEF DESCRIPTION OF THE SEQUENCES

SEQ ID NO:1 is a *B. thuringiensis* DNA sequence encoding IRDIG17912 toxin; 963 nt.
SEQ ID NO:2 is the *B. thuringiensis* IRDIG17912 protein sequence, 321 aa, encoded by SEQ ID NOs:1 and 5.
SEQ ID NO:3 is a 5' truncated DNA sequence encoding an N-terminal truncated IRDIG17912; 855 nt.
SEQ ID NO:4 is the N-terminal truncated IRDIG17912 protein sequence; 285 aa, encoded by SEQ ID NOs:3 and 6.
SEQ ID NO:5 is a maize-optimized DNA sequence encoding IRDIG17912 toxin; 963 nt.
SEQ ID NO:6 is 5' truncated maize-optimized DNA sequence encoding N-terminal truncated IRDIG17912; 855 nt.
SEQ ID NO:7 is DNA sequence encoding IRDIG17912 with a 5' sequence encoding a chloroplast transit peptide (TraP4); 1176 nt.
SEQ ID NO:8 is IRDIG17912 with (TraP4), also known as DIG-1004; 392 aa.
SEQ ID NO:9 is DNA sequence encoding IRDIG17912 with a 5' sequence encoding a chloroplast transit peptide (TraP8); 1161 nt.
SEQ ID NO:10 is IRDIG17912 with TraP8, also known as DIG-1005; 387 aa.

SEQ ID NO:11 is DNA sequence encoding truncated IRDIG17912 with mitochondria/cp transit peptide, also known as DIG-1006; 1200 nt.
SEQ ID NO:12 is IRDIG17912 with mitochondria/cp transit peptide, also known as DIG-1006; 400 aa.
SEQ ID NO:13 is a DNA sequence encoding IRDIG17912 with an ER transit peptide and N glycosylation sites removed, known as DIG-1007; 1032 nt.
SEQ ID NO:14 is IRDIG17912 with an ER transit peptide and N glycosylation sites removed, known as DIG-1007; 344 aa.
SEQ ID NO:15 is DNA sequence encoding IRDIG17912 with an ER transit peptide, an ER retention peptide and N glycosylation sites removed; 1050 nt.
SEQ ID NO:16 is IRDIG17912 with an ER transit peptide, an ER retention peptide and N glycosylation sites removed, also known as DIG-1008; 350 aa.

DETAILED DESCRIPTION OF THE INVENTION

The following words and phrases have the meanings set forth below. Unless specifically indicated, the terms "a", "an", and "the" signify "at least one" as used herein.

"An IRDIG17912 toxin" is defined as SEQ ID NOs: 2, 4, 8, 10, 12, 14 and 16, protein toxins have at least 70% sequence identity with any of the foregoing including derivatives, analogs, and mutant forms. A more preferred group of IRDIG17912 toxins consists of SEQ ID NOs: 2, 4, 8, 10, 12, 14 and 16, protein toxins have at least 80% sequence identity with any of the foregoing sequences. Another preferred group of IRDIG17912 toxins consists of SEQ ID NOs: 2, 4, 8, 10, 12, 14 and 16, protein toxins have at least 90% sequence identity with any of the foregoing sequences. Another preferred group of IRDIG17912 toxins consists of SEQ ID NOs: 2, 4, 8, 10, 12, 14 and 16, protein toxins have at least 95% sequence identity with any of the foregoing sequences. Another preferred group of IRDIG17912 toxins consists of SEQ ID NOs: 2, 4, 8, 10, 12, 14 and 16, protein toxins have at least 99% sequence identity with any of the foregoing sequences. The most preferred group of IRDIG17912 toxins consists of SEQ ID NOs: 2, 4, 8, 10, 12, 14 and 16.

"DNA segment" refers to a DNA molecule that has been isolated free of total genomic DNA of a particular species. Therefore, a DNA segment encoding a protein or peptide refers to a DNA segment that contains protein coding sequences yet is isolated away from, or purified free from, total genomic DNA of the species from which the DNA segment is obtained, which in the instant case is the genome of the Gram-positive bacterial genus, *Bacillus*, and in particular, the species known as *B. thuringiensis*. Included within the term "DNA segment", are DNA segments and smaller fragments of such segments, and also recombinant vectors, including, for example, plasmids, cosmids, phagemids, phage, viruses, and the like.

"Isolated substantially away from other coding sequences" means that the gene of interest, in this case, a gene encoding a bacterial insecticidal protein, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

"A sequence essentially as set forth in SEQ ID NO:2" means that the sequence substantially corresponds to a portion of the sequence of SEQ ID NO:2 and has relatively few amino acids that are not identical to, or a biologically functional equivalent of, the amino acids of any of these sequences. The term "biologically functional equivalent" is well understood in the art. Accordingly, sequences that have between about 70% and about 80%, or more preferably between about 81% and about 90%, or even more preferably between about 91% and about 99% amino acid sequence identity or functional equivalence to the amino acids of SEQ ID NO:2 will be sequences that are "essentially as set forth in SEQ ID NO:2."

Expression: The combination of intracellular processes, including transcription and translation undergone by a coding DNA molecule such as a structural gene to produce a polypeptide.

By the use of the term "genetic material" herein, it is meant to include all genes, nucleic acid, DNA and RNA. The term "dsRNA" refers to double-stranded RNA. For designations of nucleotide residues of polynucleotides, DNA, RNA, oligonucleotides, and primers, and for designations of amino acid residues of proteins, standard IUPAC abbreviations are employed throughout this document. Nucleic acid sequences are presented in the standard 5' to 3' direction, and protein sequences are presented in the standard amino (N) terminal to carboxy (C) terminal direction.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding the whole or a portion of the peptide sequence disclosed in SEQ ID NO:2, or that are identical to or complementary to DNA sequences which encode the peptide disclosed in SEQ ID NO:2, and particularly the DNA segment disclosed in SEQ ID NO:1. For example, DNA sequences such as about 14 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200-500; 500-1,000; 1,000-2,000; 2,000-3,000; 3,000-5,000; and up to and including sequences of about 10,000 nucleotides and the like.

It will also be understood that this invention is not limited to the particular nucleic acid sequences which encode peptides of the present invention, or which encode the amino acid sequence of SEQ ID NO:2, including the DNA sequence which is particularly disclosed in SEQ ID NO:1. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

In addition to their use in directing the expression of insecticidal proteins or peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:1 will find particular utility. Longer contiguous identical or complementary sequences, e.g., those of about 20, 30, 40, 50, 100, 200, 500, 1000, 2000, 5000, 10000 etc. (including all intermediate lengths and up to and including full-length sequences) will also be of use in certain embodiments.

The ability of such nucleic acid probes to specifically hybridize to protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10-14, 15-20, 30, 50, or even of 100-200 nucleotides or so, identical or complementary to the DNA sequence of SEQ ID NO:1, are particularly contemplated as hybridization probes for use in, e.g., Southern and Northern blotting. Smaller fragments will generally find use in hybridization embodiments, wherein the length of the contiguous complementary region may be varied, such as between about 10-14 and about 100 or 200 nucleotides, but larger contiguous complementary stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. Typically, stringent conditions will be those in which the salt concentration is less than about 1.5 M Na ion, typically about 0.01 to 1.0 M Na ion concentration (or other salts) at pH 7.0 to pH 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30% to 35% formamide, 1 M NaCl, 1% SDS (sodium dodecyl sulfate) at 37° C. and a wash in 1× to 2×SSC (20×SSC=3.0 M NaCl/0.3 M trisodium citrate) at 50° C. to 55° C. Exemplary moderate stringency conditions include hybridization in 40% to 45% formamide, 1.0 M NaCl, 1% SDS at 37° C. and a wash in 0.5× to 1×SSC at 55° C. to 60° C. Exemplary high stringency conditions include hybridization in 50% formamide, 1 M NaCl, 1% SDS at 37° C. and a wash in 0.1×SSC at 60° C. to 65° C. Optionally, wash buffers may comprise about 0.1% to about 1% SDS. Duration of hybridization is generally less than about 24 hours, usually about 4 to about 12 hours. Such selective conditions tolerate little, if any, mismatch between the probe and the template or target strand, and would be particularly suitable for isolating protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1991, are particularly relevant.

Specificity is typically the function of post-hybridization washes, the critical factors being the ionic strength and temperature of the final wash solution. For DNA/DNA hybrids, the thermal melting point ($T_m$) is the temperature (under defined ionic strength and pH) at which 50% of a complementary target sequence hybridizes to a perfectly matched probe. $T_m$ is reduced by about 1° C. for each 1% of mismatching; thus, $T_m$, hybridization conditions, and/or wash conditions can be adjusted to facilitate annealing of sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, highly stringent conditions can utilize a hybridization and/or wash at 1° C., 2° C., 3° C., or 4° C. lower than the $T_m$; moderately stringent conditions can utilize a hybridization and/or wash at 6° C., 7° C., 8° C., 9° C., or 10° C. lower than the $T_m$, and low stringency conditions can utilize a hybridization and/or wash at 11° C., 12° C., 13° C., 14° C., 15° C., or 20° C. lower than the $T_m$.

$T_m$ (in ° C.) may be experimentally determined or may be approximated by calculation. For DNA-DNA hybrids, the $T_m$ can be approximated from the equation of Meinkoth and Wahl (1984):

$$T_m(° C.)=81.5° C.+16.6(\log M)+0.41(\% GC)-0.61(\% \text{formamide})-500/L;$$

where M is the molarity of monovalent cations, % GC is the percentage of guanosine and cytosine nucleotides in the DNA, % formamide is the percentage of formamide in the hybridization solution (w/v), and L is the length of the hybrid in base pairs.

Alternatively, the $T_m$ is described by the following formula (Beltz et al., 1983).

$$T_m(° C.)=81.5° C.+16.6(\log [Na+])+0.41(\% GC)-0.61(\% \text{formamide})-600/L$$

where [Na+] is the molarity of sodium ions, % GC is the percentage of guanosine and cytosine nucleotides in the DNA, % formamide is the percentage of formamide in the hybridization solution (w:v), and L is the length of the hybrid in base pairs.

Using the equations, hybridization and wash compositions, and desired $T_m$, those of ordinary skill will understand that variations in the stringency of hybridization and wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) and Ausubel et al. (1995). Also see Sambrook et al. (1989).

Of course, for some applications, for example, where one desires to prepare mutants employing a mutant primer strand hybridized to an underlying template or where one seeks to isolate protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

The invention also discloses and claims a composition comprising a IRDIG17912 protein. The composition may comprises bacterial host cells which express a IRDIG17912 protein, in the soluble fraction, inclusion bodies or crystals containing the IRDIG17912 protein, culture supernatant, disrupted cells, cell extracts, lysates, homogenates, and the like. The compositions may be in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing insecticidal proteins are well-known to those of skill in the art of bacterial protein isolation and purification. In certain embodiments, the proteins may be purified, concentrated, admixed with other reagents, or processed to a desired final form. Preferably, the composition will comprise from about 1% to about 90% by weight of the protein, and more preferably from about 5%, to about 50% by weight.

In a preferred embodiment, the protein compositions of the invention may be prepared by a process which comprises the steps of culturing a *Bacillus thuringiensis* cell which expresses a IRDIG17912 protein under conditions effective to produce such a protein, and then obtaining the protein from the cell. The obtaining of such a protein may further include purifying, concentrating, processing, or mixing the protein with one or more reagents. Preferably, the IRDIG17912 toxin is obtained in an amount from between about 1% to about 90% by weight and more preferably from about 5% to about 50% by weight.

The invention also relates to a method of preparing a IRDIG17912 protein composition. Such a method generally involves the steps of culturing a *Bacillus thuringiensis* cell which expresses an IRDIG17912 toxin under conditions effective to produce the protein, and then obtaining the protein so produced. In a preferred embodiment the *Bacillus thuringiensis* cell is any *Bacillus thuringiensis* cell which contains a IRDIG17912 gene segment. Alternatively, the recombinant plasmid vectors of the invention may be used to transform other suitable bacterial or eukaryotic cells to produce the protein of the invention. Prokaryotic host cells including Gram-negative cells such as *E. coli, Pseudomonas fluorescens* and related Enterobacteraceae, or Gram-positive cells such as *Bacillus* spp. (including *B. megaterium, B. subtilis,* and *B. thuringiensis*) and the like are all contemplated to be useful in the preparation of the insecticidal proteins of the invention. Particularly preferred are the commonly used *E. coli* expression strains.

In such embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a protein or peptide in its natural environment. Such promoters may include promoters normally associated with other genes, and/or promoters isolated from any bacterial, viral, eukaryotic, or plant cell. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the *Pichia* expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of peptides or epitopic core regions, such as may be used to generate anti-protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NO:2.

In yet another aspect, the present invention provides methods for producing a transgenic cell, and in particular a plant or animal cell which expresses a nucleic acid segment encoding the novel IRDIG17912 protein of the present invention. The process of producing transgenic cells is well known in the art. In general, the method comprises transforming a suitable host cell with a DNA segment which contains a promoter operatively linked to a coding region that encodes an IRDIG17912 toxin. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant protein expressed in a particular transgenic cell, the invention also provides for the expression of protein antisense mRNA. The use of antisense mRNA as a means of controlling or decreasing the amount of a given protein of interest in a cell is well known in the art.

In a preferred embodiment, the invention encompasses a plant cell which has been transformed with a nucleic acid segment of the invention, and which expresses a gene or gene segment encoding one or more of the novel polypeptide compositions disclosed herein. As used herein, the term "transgenic plant cell" is intended to refer to a plant cell that has incorporated DNA sequences, including but not limited to genes which are not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of an IRDIG17912 toxin-expressing transgene. In some instances, more than one transgene will be incorporated into the genome of the transformed host plant cell. Such is the case when more than one protein-encoding DNA segment is incorporated into the genome of such a plant. In certain situations, it may be desirable to have one, two, three, four, or even more *B. thuringiensis* crystal proteins (either native or recombinantly-engineered) incorporated and stably expressed in the transformed transgenic plant. In preferred embodiments, the introduction of the transgene into the genome of the plant cell results in a stable integration wherein the offspring of such plants also contain a copy of the transgene in their genome. The inheritability of this genetic element by the progeny of the plant into which the gene was originally introduced is a preferred aspect of this invention.

A preferred gene which may be introduced includes, for example, a protein-encoding a DNA sequence from bacterial origin, and particularly one or more of those described herein which are obtained from *Bacillus* spp. Highly preferred nucleic acid sequences are those obtained from *B. thuringiensis*, or any of those sequences which have been genetically engineered to decrease or increase the insecticidal activity of the protein in such a transformed host cell.

Means for transforming a plant cell and the preparation of a transgenic cell line are well known in the art (as exemplified in U.S. Pat. Nos. 5,550,318; 5,508,468; 5,482,852; 5,384,253; 5,276,269; and 5,225,341, all specifically incorporated herein by reference), and are briefly discussed herein. Vectors, plasmids, cosmids, YACs (yeast artificial chromosomes), and DNA segments for use in transforming such cells will, of course, generally comprise either the operons, genes, or gene-derived sequences of the present invention, either native, or synthetically-derived, and particularly those encoding the disclosed proteins. These DNA or nucleic acid constructs can further include structures such as promoters, enhancers, polylinkers, or even gene sequences which have positively- or negatively-regulating activity upon the particular genes of interest as desired. The DNA segment or gene may encode either a native or modified protein, which will be expressed in the resultant recombinant cells, and/or which will impart an improved phenotype to the regenerated plant.

Such transgenic plants may be desirable for increasing the insecticidal resistance of a monocotyledonous or dicotyledonous plant, by incorporating into such a plant, a transgenic DNA segment encoding an IRDIG17912 protein which is toxic to coleopteran and lepidopteran insects. Particularly preferred plants include corn, wheat, soybeans, turf grasses, ornamental plants, fruit trees, shrubs, vegetables, grains, legumes, and the like, or any plant into which introduction of a insecticidal protein transgene is desired.

In a related aspect, the present invention also encompasses a seed produced by the transformed plant, a progeny from such seed, and a seed produced by the progeny of the original transgenic plant, produced in accordance with the above process. Such progeny and seeds will have a protein encoding transgene stably incorporated into its genome, and such progeny plants will inherit the traits afforded by the introduction of a stable transgene in Mendelian fashion. All such transgenic plants having incorporated into their genome transgenic DNA segments encoding an IRDIG17912 toxin are aspects of this invention.

In particular embodiments, the inventors contemplate the use of antibodies, either monoclonal or polyclonal which bind to the proteins disclosed herein. Means for preparing and characterizing antibodies are well known in the art (See, e.g, Harlow and Lane, 1988).

The present invention also provides compositions, methods and kits for screening samples suspected of containing an IRDIG17912 toxin or a gene encoding such a toxin. Such screening may be performed on samples such as transformed host cells, transgenic plants, progeny or seed thereof, or laboratory samples suspected of containing or producing such a polypeptide or nucleic acid segment. A kit can contain a novel nucleic acid segment or an antibody of the present invention. The kit can contain reagents for detecting an interaction between a sample and a nucleic acid or an antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

In still further embodiments, the present invention concerns immunodetection methods and associated kits. It is proposed that the proteins or peptides of the present invention may be employed to detect antibodies having reactivity therewith, or, alternatively, antibodies prepared in accordance with the present invention, may be employed to detect proteins or protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a protein or peptide or a protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of proteins or related peptides and/or antibodies in a sample. Samples may include cells, cell supernatants, cell suspensions, cell extracts, enzyme fractions, protein extracts, or other cell-free compositions suspected of containing proteins or peptides. Generally speaking, kits in accordance with the present invention will include a suitable protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

ELISAs and Immunoprecipitation.

ELISAs may be used in conjunction with the invention. In an ELISA assay, proteins or peptides incorporating protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/TWEEN® surface active agent (ICI Americas, Inc., Wilmington, Del.). These added agents also tend to assist in the reduction of nonspecific background. The layered antisera is then allowed to incubate for from about 2 to about 4 hours, at temperatures preferably on the order of about 25° to about 27° C. Following incubation, the antisera-contacted surface is washed so as to remove non-immunocomplexed material. A preferred washing procedure includes washing with a solution such as PBS/TWEEN® surface active agent, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS/TWEEN®) surface active agent.

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-protein antibodies of the present invention are particularly useful for the isolation of other protein antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Non-ionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

The compositions of the present invention will find great use in immunoblot or western blot analysis. The anti-peptide antibodies may be used as high-affinity primary reagents for the identification of proteins immobilized onto a solid support matrix, such as nitrocellulose, nylon or combinations thereof. In conjunction with immuno-precipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

The present invention is also directed to protein or peptide compositions, free from total cells and other peptides, which comprise a purified protein or peptide which incorporates an epitope that is immunologically cross-reactive with one or more anti-protein antibodies. In particular, the invention concerns epitopic core sequences derived from insecticidal proteins or peptides.

As used herein, the term "incorporating an epitope(s) that is immunologically cross-reactive with one or more anti-protein antibodies" is intended to refer to a peptide or protein antigen which includes a primary, secondary, or tertiary structure similar to an epitope located within a protein or polypeptide. The level of similarity will generally be to such a degree that monoclonal or polyclonal antibodies directed against the protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of Cry immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, e.g., Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to proteins, and in particular insecticidal and insecticidal-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

The inventors contemplate that the protein compositions disclosed herein will find particular utility as insecticides for topical and/or systemic application to field crops, grasses, fruits and vegetables, and ornamental plants. In a preferred embodiment, the bioinsecticide composition comprises an oil flowable suspension of bacterial cells which expresses a novel protein disclosed herein. Preferably the cells are *B. thuringiensis*, however, any such bacterial host cell expressing the novel nucleic acid segments disclosed herein and producing a protein is contemplated to be useful, such as *B. megaterium, B. subtilis, E. coli*, or *Pseudomonas* spp.

In another important embodiment, the bioinsecticide composition comprises a water dispersible granule. This granule comprises bacterial cells which expresses a novel protein disclosed herein. Preferred bacterial cells are *B. thuringiensis* cells, however, bacteria such as *B. megaterium, B. subtilis, E. coli*, or *Pseudomonas* spp. cells transformed with a DNA segment disclosed herein and expressing the protein are also contemplated to be useful.

In a third important embodiment, the bioinsecticide composition comprises a wettable powder, dust, pellet, or collodial concentrate. This powder comprises bacterial cells which expresses a novel protein disclosed herein. Preferred bacterial cells are *B. thuringiensis* cells, however, bacteria such as *B. megaterium, B. subtilis, E. coli*, or *Pseudomonas* spp. cells transformed with a DNA segment disclosed herein and expressing the protein are also contemplated to be useful. Such dry forms of the insecticidal compositions may be formulated to dissolve immediately upon wetting, or alternatively, dissolve in a controlled-release, sustained release, or other time-dependent manner.

In a fourth important embodiment, the bioinsecticide composition comprises an aqueous suspension of bacterial cells such as those described above which express the protein. Such aqueous suspensions may be provided as a concentrated stock solution which is diluted prior to application, or alternatively, as a diluted solution ready-to-apply.

For these methods involving application of bacterial cells, the cellular host containing the protein gene(s) may be grown in any convenient nutrient medium, where the DNA construct provides a selective advantage, providing for a selective medium so that all or substantially all of the cells retain the *B. thuringiensis* gene. These cells may then be harvested in accordance with conventional ways. Alternatively, the cells can be treated prior to harvesting.

When the insecticidal compositions comprise intact *B. thuringiensis* cells expressing the protein of interest, such bacteria may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel IRDIG17912 or IRDIG17912-derived toxin may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate crystals and/or spores from bacterial cultures expressing the protein and apply solutions, suspensions, or collodial preparations of such crystals and/or spores as the active bioinsecticidal composition.

Regardless of the method of application, the amount of the active component(s) are applied at an insecticidally-effective amount, which will vary depending on such factors as, for example, the specific coleopteran or lepidopteran insects to be controlled, the specific plant or crop to be treated, the environmental conditions, and the method, rate, and quantity of application of the insecticidally-active composition.

The insecticide compositions described may be made by formulating the bacterial cell, crystal and/or spore suspension, or isolated protein component with the desired agriculturally-acceptable carrier. The compositions may be formulated prior to administration in an appropriate means such as lyophilized, freeze-dried, dessicated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insecticidal compositions of this invention are applied to the environment of the target coleopteran or lepidopteran insect, typically onto the foliage of the plant or crop to be protected, by conventional methods, preferably by spraying. The strength and duration of insecticidal application will be set with regard to conditions specific to the particular pest(s) and crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition which is used for environmental, systemic, or foliar application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight.

The insecticidal formulation may be administered to a particular plant or target area in one or more applications as needed, with a typical field application rate per hectare ranging on the order of from about 50 g to about 500 g of active ingredient, or of from about 500 g to about 1000 g, or of from about 1000 g to about 5000 g or more of active ingredient.

Modification and changes may be made in the primary structure of the toxins of the present invention to produce derivatives, analogs and mutants and DNA segments which encode them and still obtain a functional insecticidal molecule that encodes a protein or peptide with desirable characteristics. In particular embodiments of the invention, mutated proteins are contemplated to be useful for increasing the insecticidal activity of the protein, and consequently increasing the insecticidal activity and/or expression of the recombinant transgene in a plant cell. The amino acid changes may be achieved by changing the codons of the DNA sequence, according to the codons given in Table 1.

TABLE 1

| Amino Acids | Abbreviation | Abbreviation | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules for example, enzymes, substrates, receptors, DNA, antibodies, antigens, and the like.

Each amino acid has been assigned a hydropathic index on the basis of their hydrophobicity and charge characteristics (Kyte and Doolittle, 1982). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected protein gene sequence, e.g., a sequence such as that shown in SEQ ID NO:1. The ability of such nucleic acid probes to specifically hybridize to a protein-encoding gene sequence lends them particular utility in a variety of embodiments. Most importantly, the probes may be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a protein gene from *B. thuringiensis* using PCR™ technology. Segments of related protein genes from other species may also be amplified by PCR™ using such primers.

The present invention contemplates an expression vector comprising a polynucleotide of the present invention. Thus, in one embodiment an expression vector is an isolated and purified DNA molecule comprising a promoter operatively linked to a coding region that encodes a polypeptide of the present invention, which coding region is operatively linked to a transcription-terminating region, whereby the promoter drives the transcription of the coding region.

As used herein, the term "operatively linked" means that a promoter is connected to a coding region in such a way that the transcription of that coding region is controlled and regulated by that promoter. Means for operatively linking a promoter to a coding region are well known in the art.

In a preferred embodiment, the recombinant expression of DNAs encoding the proteins of the present invention is preferable in a *Bacillus* host cell. Preferred host cells include *B. thuringiensis, B. megaterium, B. subtilis*, and related bacilli, with *B. thuringiensis* host cells being highly preferred. Promoters that function in bacteria are well-known in the art. An exemplary and preferred promoter for the *Bacillus* crystal proteins include any of the known crystal protein gene promoters, including the IRDIG17912 gene promoter, and promoters specific for *B. thuringiensis* sigma factors, such as $\sigma^E$ and $\sigma^K$ (for a review see Baum and Malvar, 1995) Alternatively, mutagenized or recombinant crystal protein-encoding gene promoters may be engineered by the hand of man and used to promote expression of the novel gene segments disclosed herein.

In an alternate embodiment, the recombinant expression of DNAs encoding the proteins of the present invention is performed using a transformed Gram-negative bacterium such as an *E. coli* or *Pseudomonas* spp. host cell. Promoters which function in high level expression of target polypeptides in *E. coli* and other Gram-negative host cells are also well known in the art.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue-specific or developmentally specific promoters affecting dicots or monocots.

Regardless of transformation technique, the gene is preferably incorporated into a gene transfer vector adapted to express the B.t. insecticidal toxin genes and variants in the plant cell by including in the vector a plant promoter. In addition to plant promoters, promoters from a variety of sources can be used efficiently in plant cells to express foreign genes. For example, promoters of bacterial origin, such as the octopine synthase promoter, the nopaline synthase promoter, the mannopine synthase promoter; promoters of viral origin, such as the 35S and 19S promoters of cauliflower mosaic virus (CaMV), and the like may be used. Plant-derived promoters include, but are not limited to ribulose-1,6-bisphosphate (RUBP) carboxylase small subunit (ssu), beta-conglycinin promoter, phaseolin promoter, ADH (alcohol dehydrogenase) promoter, heat-shock promoters, ADF (actin depolymerization factor) promoter, and tissue specific promoters. Promoters may also contain certain enhancer sequence elements that may improve the transcription efficiency. Typical enhancers include but are not limited to ADH1-intron 1 and ADH1-intron 6. Constitutive promoters may be used. Constitutive promoters direct continuous gene expression in nearly all cells types and at nearly all times (e.g., actin, ubiquitin, CaMV 35S). Tissue specific promoters are responsible for gene expression in specific cell or tissue types, such as the leaves or seeds (e.g., zein, oleosin, lectin, napin, ACP (Acyl Carrier Protein)), and these promoters may also be used. Promoters may also be used that are active during a certain stage of the plants' development as well as active in specific plant tissues and organs. Examples of such promoters include but are not limited to promoters that are root specific, pollen specific, embryo specific, corn silk specific, cotton fiber specific, seed endosperm specific, phloem specific, and the like.

Exemplary tissue-specific promoters are corn sucrose synthetase 1 (Yang et al., 1990), corn alcohol dehydrogenase 1 (Vogel et al., 1989), corn light harvesting complex (Simpson, 1986), corn heat shock protein (Odell et al., 1985), pea small subunit RuBP Carboxylase (Poulsen et al., 1986; Cashmore et al., 1983), Ti plasmid mannopine synthase (Langridge et al., 1989), Ti plasmid nopaline synthase (Langridge et al., 1989), *petunia* chalcone isomerase (Van Tunen et al., 1988), bean glycine rich protein 1 (Keller et al., 1989), CaMV 35s transcript (Odell et al., 1985) and Potato patatin (Wenzler et al., 1989). Preferred promoters are the cauliflower mosaic virus (CaMV 35S) promoter and the S-E9 small subunit RuBP carboxylase promoter.

Under certain circumstances it may be desirable to use an inducible promoter. An inducible promoter is responsible for expression of genes in response to a specific signal, such as: physical stimulus (e.g., heat shock genes); light (e.g., RUBP carboxylase); hormone (e.g., glucocorticoid); antibiotic (e.g., tetracycline); metabolites; and stress (e.g., drought). Other desirable transcription and translation elements that function in plants may be used, such as 5' untranslated leader sequences, RNA transcription termination sequences and poly-adenylate addition signal sequences. Numerous plant-specific gene transfer vectors are known to the art.

An expression vector containing a coding region that encodes a polypeptide of interest may be engineered to be under control of the lectin promoter. Such a vector may be introduced into plants using, for example, a protoplast transformation method (Dhir et al., 1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described (Rogers et al., 1987). However, several other plant integrating vector systems are known to function in plants including pCaMVCN transfer control vector described (Fromm et al., 1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II (nptII) and nopaline synthase 3' non-translated region described (Rogers et al., 1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer insecticidal activity to a cell is preferably an IRDIG17912 toxin-encoding gene.

A bacterium, a yeast cell, plant cell, or a plant transformed with an expression vector of the present invention is also contemplated. A transgenic bacterium, yeast cell, plant cell, or plant derived from such a transformed or transgenic cell is also contemplated. Means for transforming bacteria and yeast cells are well known in the art. Typically, means of transformation are similar to those well known means used to transform other bacteria or yeast such as *E. coli* or *Saccharomyces cerevisiae*.

Methods for DNA transformation of plant cells include *Agrobacterium*-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

There are many methods for introducing transforming DNA segments into cells, but not all are suitable for delivering DNA to plant cells. Suitable methods are believed to include virtually any method by which DNA can be introduced into a cell, such as by *Agrobacterium* infection, direct delivery of DNA such as, for example, by PEG-mediated transformation of protoplasts (Omirulleh et al., 1993), by desiccation/inhibition-mediated DNA uptake, by electroporation, by agitation with silicon carbide fibers, by acceleration of DNA coated particles, etc. In certain embodiments, acceleration methods are preferred and include, for example, microprojectile bombardment and the like.

Technology for introduction of DNA into cells is well known to those of skill in the art. Four general methods for delivering a gene into cells have been described: (1) chemical methods (Graham and van der Eb, 1973; Zatloukal et al., 1992); (2) physical methods such as microinjection (Capecchi, 1980), electroporation (Wong and Neumann, 1982; Fromm et al., 1985) and the gene gun (Johnston and Tang, 1994; Fynan et al., 1993); (3) viral vectors (Clapp, 1993; Lu et al., 1993; Eglitis and Anderson, 1988a; 1988b); and (4) receptor-mediated mechanisms (Curiel et al., 1991; 1992; Wagner et al., 1992).

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced insecticidal activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts is described in (Fujimura et al., 1985; Toriyama et al., 1986; Yamada et al., 1986; Abdullah et al., 1986).

To transform plant strains that cannot be successfully regenerated from protoplasts, other ways to introduce DNA into intact cells or tissues can be utilized. For example, regeneration of cereals from immature embryos or explants can be effected as described (Vasil, 1988). In addition, "particle gun" or high-velocity microprojectile technology can be utilized (Vasil, 1992).

Using that latter technology, DNA is carried through the cell wall and into the cytoplasm on the surface of small metal particles as described (Klein et al., 1987; Klein et al., 1988; McCabe et al., 1988). The metal particles penetrate through several layers of cells and thus allow the transformation of cells within tissue explants.

By transforming a suitable host cell, such as a plant cell, with a recombinant IRDIG17912 encoding gene-containing segment, the expression of the encoded protein (i.e., a bacterial protein or polypeptide having insecticidal activity against coleopterans and/or lepidopterans) can result in the formation of insect-resistant plants.

By way of example, one may utilize an expression vector containing a coding region for a *B. thuringiensis* protein and an appropriate selectable marker to transform a suspension of embryonic plant cells, such as wheat or corn cells using a method such as particle bombardment (Maddock et al., 1991; Vasil et al., 1992) to deliver the DNA coated on microprojectiles into the recipient cells. Transgenic plants are then regenerated from transformed embryonic calli that express the insecticidal proteins.

The formation of transgenic plants may also be accomplished using other methods of cell transformation which are known in the art such as *Agrobacterium*-mediated DNA transfer (Fraley et al., 1983). Alternatively, DNA can be introduced into plants by direct DNA transfer into pollen (Zhou et al., 1983; Hess, 1987; Luo et al., 1988), by injection of the DNA into reproductive organs of a plant (Pena et al., 1987), or by direct injection of DNA into the cells of immature embryos followed by the rehydration of desiccated embryos (Neuhaus et al., 1987; Benbrook et al., 1986).

The regeneration, development, and cultivation of plants from single plant protoplast transformants or from various transformed explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A transgenic plant of this invention thus has an increased amount of a coding region (e.g., an insecticidal gene) that encodes the polypeptide of interest. A preferred transgenic plant is an independent segregant and can transmit that gene and its activity to its progeny. A more preferred transgenic plant is homozygous for that gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for, by way of example, increased insecticidal capacity against coleopteran and/or lepidopteran insects, preferably in the field, under a range of environmental conditions. The inventors contemplate that the present invention will find particular utility in the creation of transgenic plants of commercial interest including various turf grasses, wheat, corn, rice, barley, oats, a variety of ornamental plants and vegetables, as well as a number of nut- and fruit-bearing trees and plants.

All patents, patent applications, provisional applications, and publications referred to or cited herein are incorporated by reference in their entirety to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

All percentages are by weight and all solvent mixture proportions are by volume unless otherwise noted. All temperatures are in degrees Celsius.

Example 1

Isolation of the Gene Encoding IRDIG17912 Insecticidal Protein

A nucleic acid encoding the insecticidal protein designated herein as IRDIG17912 was isolated from B.t. strain PS28Q3. Forward and reverse primers for Polymerase Chain Reaction (PCR) were designed and used to amplify SEQ ID NO:1 a 963 bp nucleotide sequence encoding the full-length IRDIG17912 protein. The amplified fragment was subcloned into a protein expression vector backbone. SEQ ID NO:2 is the 321 amino acid sequence of the full-length IRDIG17912 protein deduced from SEQ ID NO:1.

Standard cloning methods were used in the construction of Pseudomonas fluorescens (Pf) expression plasmids engineered to produce full-length IRDIG17912 toxins encoded by native and plant-optimized coding regions (described below). Restriction endonucleases were obtained from New England BioLabs (NEB; Ipswich, Mass.) and T4 DNA Ligase (NEB; Ipswich, Mass.) was used for DNA ligation. DNA fragments were purified using a QIAquick® Gel Extraction Kit (Qiagen, Venio, Limburg) after agarose Tris-acetate gel electrophoresis. Plasmid preparations were performed using the NucleoSpin® Plasmid Kit (Macherey-Nagel Inc, Bethlehem, Pa.) following the instructions of the suppliers for low-copy plasmid purification or the Qiagen Plasmid Plus Midi Kit® (Qiagen, Hilden, Germany).

Example 2

Design of a Plant Codon-Optimized IRDIG17912 Gene

One skilled in the art of plant molecular biology will understand that multiple DNA sequences may be designed to encode a single amino acid sequence. A common means of increasing the expression of a coding region for a protein of interest is to tailor the coding region in such a manner that its codon composition resembles the overall codon composition of the host in which the gene is destined to be expressed. Guidance regarding the design and production of synthetic genes can be found in, for example, WO1997013402, U.S. Pat. Nos. 6,166,302, and 5,380,831.

A DNA sequence having a maize codon bias was designed and synthesized to produce an IRDIG17912 insecticidal protein in transgenic monocot plants. A codon usage table for maize (Zea mays L.) was calculated from hundreds of protein coding sequences obtained from sequences deposited in GenBank (www.ncbi.nlm.nih.gov). A rescaled maize codon set was calculated after omitting any synonymous codon used less than about 10% of total codon uses for that amino acid.

An additional IRDIG17912 DNA coding sequence (SEQ ID NO:3) that encodes an amino terminal truncated IRDIG17912 protein was altered by codon substitutions to make a maize-codon-optimized DNA sequence encoding the IRDIG17912 truncated protein toxin. The resulting DNA sequence had the overall codon composition of the maize-optimized codon bias table. Further refinements of the sequences were made to eliminate undesirable restriction enzyme recognition sites, potential plant intron splice sites, long runs of A/T or C/G residues, and other motifs that might interfere with mRNA stability, transcription, or translation of the coding region in plant cells. Other changes were made to introduce desired restriction enzyme recognition sites, and to eliminate long internal Open Reading Frames (frames other than +1). These changes were all made within the constraints of retaining the maize-biased Rescaled codon composition. The maize-optimized DNA sequences encoding IRDIG17912 full length and truncated toxins are disclosed as SEQ ID NO:5 and SEQ ID NO:6.

The foregoing provides several embodiments of the isolated polynucleotide according to the invention, including polynucleotides that are codon-optimized for expression of IRDIG17912 insecticidal toxin polypeptides of the invention.

Example 3

Construction of Expression Plasmid Encoding IRDIG17912 Toxin in Bacterial Hosts

Standard cloning methods were used in the construction of Pseudomonas fluorescens (Pf) expression plasmids engineered to produce the IRDIG17912 toxin encoded by either the native or the maize-optimized coding sequences. Restriction endonucleases were obtained from New England BioLabs (NEB; Ipswich, Mass.) and T4 DNA Ligase (Invitrogen) was used for DNA ligation. Plasmid preparations were performed using the NucleoSpin® Plasmid Kit (Macherey-Nagel Inc, Bethlehem, Pa.) following the instructions of the supplier. DNA fragments were purified using the QIAQUICK Gel Extraction kit (Qiagen) after agarose Trisacetate gel electrophoresis. The linearized vector was treated with Antarctic Phosphatase (NEB) to enhance formation of recombinant molecules.

A DNA fragment having the IRDIG17912 coding sequence (CDS), as provided by SEQ ID NO:5, was subcloned into pDOW1169 at restriction sites, whereby IRDIG17912 CDS was placed under the expression control of the Ptac promoter and the rrnBT1T2 terminator from plasmid pKK223-3 (PL Pharmacia, Milwaukee, Wis.). pDOW1169 is a low copy plasmid with the RSF1010 origin of replication, a pyrF gene, and a ribosome binding site preceding the restriction enzyme recognition sites into which DNA fragments containing protein coding regions may be introduced (U.S. Pat. No. 7,618,799). The expression plasmid (pDAB 120852) was transformed by electroporation into DC454 (a near wild-type *P. fluorescens* strain having mutations ΔpyrF and lsc::lacIQI), or derivatives thereof, recovered in SOC-Soy hydrolysate medium, and plated on selective medium (M9 glucose agar lacking uracil, Sambrook et al., supra). The transformation and selection methods are generally described available in Squires et al. (2004), US Patent Application No. 20060008877, U.S. Pat. No. 7,681,799, and US Patent Application No. 20080058262, incorporated herein by reference. Recombinant colonies were identified by restriction digestion of miniprep plasmid DNA.

Example 4

Preparation of IRDIG17912 Protein Samples

Production of IRDIG17912 for characterization and insect bioassay was accomplished by shake-flask-grown *P. fluorescens* strain harboring expression construct strain DPf40092. Stored glycerol stocks of the strain were used to inoculate defined production medium with 9.5% glycerol (Teknova Catalog No. 3D7426, Hollister, Calif.). Expression of the IRDIG17912 gene was induced by addition of isopropyl-β-D-1-thiogalactopyranoside (IPTG) after an initial incubation of 24 hours at 30° C. with shaking. Cultures were sampled at the time of induction and at various times post-induction. Cell density was measured by optical density at 600 nm ($OD_{600}$). Other culture media suitable for growth of *Pseudomonas fluorescens* may also be utilized, for example, as described in Huang et al. 2007 and US Patent Application No. 20060008877. The IRDIG17912 protein accumulated in the insoluble fraction of lysed cells as inclusion bodies (IB). The recombinant insecticidal protein was enriched by isolating the IB pellet after cell lysis using centrifugation, IB were resuspended and repeatedly washed by resuspension in lysis buffer until the supernatant became colorless and the IB pellet became firm and off-white in color. The final pellet was washed, resuspended in sterile-filtered distilled water containing 2 mM EDTA, and stored at −80° C.

IRDIG17912 protein purified from the IB preparations was analyzed by SDS-PAGE. Two bands were detected, a band at ~36.7 kDa and one at 32.3 kDa, both bands were identified as IRDIG17912 by MALDI and N-terminal sequencing. The 32.3 kDa band had an N-terminus beginning at methionine 37 of SEQ ID NO: 2. The ratio of the bands to one another was approximately 1:1. Quantification of target bands was done by comparing densitometric values for the bands against bovine serum albumin (BSA) samples run on the same gel to generate a standard curve.

Example 5

Insecticidal Activity of IRDIG17912 Protein

IRDIG17912 was tested and found to have insecticidal activity on larvae of the coleopteran insect, the western corn rootworm (*Diabrotica virgifera virgifera* LeConte) and the lepidopteran insect, the diamondback moth (*Plutella xylostella* (Linnaeus)).

Test insects were second instar (3-4 day after eclosion) diamond back moth (DBM), *Plutella xylostella* (Linnaeus) and first instar (24-48 hr after eclosion) western corn rootworm (WCR), *Diabrotica virgifera virgifera*. DBM eggs were received from Benzon Research, Carlisle, Pa. Non-diapausing *Diabrotica virgifera virgifera* eggs (Crop Characteristics, Inc., Farmington, Minn.) were incubated for 10 days at 28° C. and 60% RH. Black head eggs were surface sterilized with 10% formalin following the method by Pleau et al. (2002). Lepidopteran test insects comprised of fall armyworm (FAW), *Spodoptera frugiperda* (J. E. Smith), corn earworm (CEW), *Heliothis zea* (Boddie) and European corn borer (ECB), *Ostrinia nubilalis* (Hubner).

The diet surface (0.263 cm$^2$) on each well was treated with 20 μL aliquots of aqueous solubilized protein or control solutions (Table 2) respectively. Treated plates were air-dried in a fume hood. Each well was infested with an individual larva and enclosed using sheets of clear and vented plastic which were heat sealed (HS4-54SLT-100, Phenix Research Products, Candler, N.C.). Eight larvae were respectively exposed to each sample in the 96-well formats. Both bioassay formats were held under controlled environmental conditions (28° C., 60% RH, 16:8 [Light:Dark] photoperiod) for 5 days. Insects were recorded as either dead or moribund. A moribund insect was one that was alive but was significantly stunted by at least 50% when visually compared with its negative control counterparts. Data is reported as a ratio of experimental units with larvae that were dead or equal to 50% or smaller in size compared to the negative control over the total experimental units tested per treatment.

TABLE 2

List of positive and negative controls.

| Controls | WCR bioassay | Lepidopteran bioassay |
| --- | --- | --- |
| Positive | Cry34/35Ab1, 100 μg/cm$^2$ | Cry1Fa, 120 ng/cm$^2$<br>Cry1Ac 30 ng/cm$^2$ |
| Negative | 10 mM CAPS buffer (pH 10)<br>20 mM Na Citrate, pH 3.5<br>BSA 100 μg/cm$^2$<br>PBS buffer, pH 7<br>Cry1Fa, 120 ng/cm$^2$<br>Cry1Ac ng/cm$^2$ | 10 mM CAPS buffer (pH 10)<br>20 mM Na Citrate, pH 3.5<br>BSA 100 μg/cm$^2$<br>PBS buffer, pH 7<br>Cry34/35Ab1, 120 ng/cm$^2$ |

Proteins were bioassayed using a 24-well WCR bioassay format. In this assay, non-diapausing WCR eggs (Crop Characteristics Inc., Farmington, Minn.) were incubated at 28° C. in soil for 10 days. These eggs were washed from the soil with water, surface sterilized with 10% formaldehyde and triple rinsed with sterile water (Pleau et al., 2002). These eggs were hatched and fed with a Dow AgroSciences proprietary WCR diet. An overlay diet bioassay was conducted in 24-well titer plates with each well containing 1.5 ml of the artificial WCR diet. Each test aliquot was pipetted at 80 uL/well onto diet surface (1.9 cm$^2$) of 4 wells and dried under room temperature in a laminar flow. The treated diet surface of each well was infested with five *D. virgifera* neonates (24-48 hr old) and test insects were enclosed in the bioassay arena with Breathe Easy® gas permeable sealing membrane for micro titer plates (USA Scientific, Orlando, Fla.). Negative controls were 20 mM sodium citrate buffer, pH 3.5; 10 mM CAPS buffer, pH 10.5; and 350 ug/cm$^2$ Cry1Fa in CAPS buffer, the positive control was 100 ug/cm$^2$ Cry34/35Ab1 in sodium citrate buffer.

Bioassay plates were held under controlled environmental conditions (28° C., 24-h scotophase, 60-80% relative humidity) for 5 days. The number of live and dead insects, as well as pooled live weight per treatment were recorded. Percent mortality and growth inhibition were calculated. Growth inhibition was calculated as follows:

$$GI=[1-(TWIT/TNIT)/(TWIBC/TNIBC)]$$

where TWIT is the Total Weight of Insects in the Treatment, TNIT is the Total Number of Insects in the Treatment, TWIBC is the Total Weight of Insects in the Background Check (Buffer control), and TNIBC is the Total Number of Insects in the Background Check (Buffer control). Control mortality did not exceed 20%. Bioassays were conducted under randomized complete block design and replicated at least 4 times, with 20 *D. virgifera virgifera* larvae per replicate.

Table 3 shows the results of a WCR bioassay in 96-well format. Data is reported as a ratio of experimental units with larvae that were dead or equal to 50% or smaller in size compared to the negative control over the total experimental units tested per treatment.

TABLE 3

| Treatment | Test 1 | Test 2 | Test 3 | Test 4 | Test 5 |
|---|---|---|---|---|---|
| IRDIG17912 | 0.833 | 1.0 | 0.5 | 0.167 | 0.833 |
| 10 mM CAPS, pH 10 | 0.083 | 0 | 0 | 0 | 0 |
| Cry34/35Ab1 100 μg/cm$^2$ | 0.917 | 0.833 | 1.0 | 1.0 | 1.0 |
| BSA 100 μg/cm$^2$ | 0.083 | 0 | 0 | 0 | 0.167 |
| Cry1Ac 30 ng/cm$^2$ | 0 | 0 | 0.167 | 0.083 | 0 |
| Cry1Fa 120 ng/cm$^2$ | 0 | 0.083 | 0.167 | 0 | 0.167 |
| PBS | 0 | 0.167 | 0 | 0 | 0 |
| 20 mM Na Citrate, pH 3.5 | 0 | 0.083 | 0 | 0 | 0 |

Table 4 shows the activity of IRIRDIG17912.1 against WCR that was confirmed in the 24-well format bioassay. Neonates of WCR were exposed to 62 μg/cm$^2$Cry34/35Ab1, and 46 μg/cm$^2$ IRIRDIG17912.1. Significantly greater percent larval mortality was exhibited from IRDIG17912.1 compared with Cry34/35Ab1. Percent growth inhibition from both IRIRDIG17912.1 and Cry34/35Ab1 was comparable.

TABLE 4

| Treatment | Dose (μg/$cm^2$) | Number of Insects Tested | Percent Mortality | GI (%) |
|---|---|---|---|---|
| IRDIG17912 | 46 | 120 | 36.05 (A) | 92.82 (A) |
| Cry34/35Ab1 (Positive Control) | 62 | 120 | 12.18 (B) | 89.98 (A) |
| Control | 0 | 120 | 0.8 (B) | 0 (B) |

Means followed by the same letter within each column are not significantly different according to Tukey HSD ($p>0.05$).

TABLE 5

IRDIG17912 dose response against WCR in a 24 well bioassay.

| Sample Name | application dose (μg/$cm^2$) | No. tested | % Mortality | GI |
|---|---|---|---|---|
| IRDIG17912 | 50 | 40 | 60 | 0.89 |
| IRDIG17912 | 30 | 37 | 57 | 0.881 |
| IRDIG17912 | 20 | 38 | 42 | 0.753 |
| IRDIG17912 | 10 | 39 | 26 | 0.561 |
| IRDIG17912 | 5 | 20 | 5 | 0.145 |
| | Controls: | | | |
| Cry1Fa | 350 | 40 | 0.000 | 0.055 |
| Cry 34/35Ab1 | 100 | 40 | 78 | 0.966 |
| 10 mM CAPS, pH 10 | 0 | 40 | 3 | 0.000 |
| 20 mM NaCitrate pH 3.5 | 0 | 40 | 0.000 | 0.000 |

IRDIG17912 protein was also tested against WCR field insects from Rudd, Floyd, Iowa as well as Bratsburg, Minn. The results of this bioassay are shown in Table 6.

Table 6 shows the sensitivity of WCR field insect strains (IA and MN) to Cry34/35Ab1 and IRDIG17912. Trypsin activated Cry3Aa protein was used as a bench mark for tolerance against Cry3 protein. ND-WCR is a non-diapause WCR (Crop Characteristics LLC) and was used as a susceptible insect strain control.

TABLE 6

| Treatment | Dose ug/$cm^2$ | Insect strain | N | Mean Avg live weight (mg) ± SEM* | Mean % larval mort ± SEM* | Mean % GI ± SEM* |
|---|---|---|---|---|---|---|
| 10 mM CAPS, pH10 | 0 | ND-WCR | 12 | 0.55 ± 0.04 A | 9.1 ± 3 A | 0 ± 0 |
| | 0 | IA | 8 | 0.68 ± 0.04 A | 1.9 ± 0.9A | 0 ± 0 |
| | 0 | MN | 8 | 0.62 ± 0.03 A | 2.7 ± 2.1 A | 0 ± 0 |
| 20 mM NaCitrate, pH3.5 | 0 | ND-WCR | 12 | 0.49 ± 0.03 AB | 3.1 ± 1 A | 0 ± 0 |
| | 0 | IA | 8 | 0.55 ± 0.05 A | 3.8 ± 3.8 A | 0 ± 0 |
| | 0 | MN | 8 | 0.50 ± 0.02 AB | 4.1 ± 2.3 A | 0 ± 0 |
| Cry3 (truncated) | 350 | ND-WCR | 12 | 0.35 ± 0.06 AB | 50.5 ± 2.6 A | 66.3 ± 4.3 A |
| | 350 | IA | 8 | 0.50 ± 0.05 A | 3.2 ± 0.9 C | 25.6 ± 7.7 B |
| | 350 | MN | 7 | 0.45 ± 0.01 AB | 5.3 ± 2 BC | 28.0 ± 3 B |

TABLE 6-continued

| Treatment | Dose ug/cm² | Insect strain | N | Mean Avg live weight (mg) ± SEM* | Mean % larval mort ± SEM* | Mean % GI ± SEM* |
|---|---|---|---|---|---|---|
| Cry34/35Ab1 | 100 | ND-WCR | 12 | 0.02 ± 0.01 A | 96.9 ± 1 A | 99.7 ± 0.3 A |
|  | 100 | IA | 8 | 0.05 ± 0.01 A | 53.3 ± 9.6 C | 95.3 ± 1.4 B |
|  | 100 | MN | 8 | 0.06 ± 0.02 A | 69.2 ± 4.4 BC | 96.6 ± 0.9 AB |
| IRDIG17912 | 100 | ND-WCR | 4 | 0.01 ± 0 B | 97.5 ± 1.4 A | 100 ± 0 A |
|  | 100 | IA | 4 | 0.14 ± 0.03 A | 78.3 ± 5.7 AB | 95.7 ± 1 A |
|  | 100 | MN | 4 | 0.10 ± 0.02 AB | 71.7 ± 6.3 AB | 94.1 ± 3.1 A |
| IRDIG17912 | 50 | ND-WCR | 4 | 0.00 ± 0 B | 97.5 ± 2.5A | 100 ± 0 A |
|  | 50 | IA | 4 | 0.10 ± 0.01 AB | 66.7 ± 2.7 B | 94.3 ± 1 A |
|  | 50 | MN | 4 | 0.12 ± 0.03 A | 66.7 ± 4.7 B | 92.2 ± 3.5 A |

*SEM - Standard Error of the Mean. Means followed by the same letter within each column and sample type are not significantly different according to Tukey HSD (p > 0.05).

Enriched IRDIG17912 from inclusion bodies was tested on lepidopteran insects, methods similar to the DBM insect bioassays were followed for corn earworm (CEW), European corn borer (ECB), and fall armyworm (FAW). IRDIG17912 insecticidal toxin did not demonstrate activity against *Euschistus heros* (Brown stink Bug (BSB)), Chrysodeixis includes (Soybean Looper (SBL)), *Helicoverpa zea* (Corn Earworm (CEW)), *Spodoptera frugiperda* (Fall armyworm (FAW)), or *Ostrinia nubilalis* (European Corn Borer (ECB)).

Table 7 shows the results of Lepidopteran insect spp. bioassays when exposed to various controls. Data is reported as a ratio of experimental units with larvae that were dead or equal to 50% or smaller in size compared to the negative control over the total experimental units tested per treatment.

TABLE 7

| Treatment & Dose | Control (positive/negative) | DBM | CEW | ECB | FAW | CEW | ECB | FAW |
|---|---|---|---|---|---|---|---|---|
| IRDIG17912 10 mM CAPS, pH 10 | negative | 1.0 0.083 | 0 0 | 0 0 | 0.167 0.167 | 0 0 | 0.167 0 | 0.167 0 |

TABLE 7-continued

| Treatment & Dose | Control (positive/negative) | DBM | CEW | ECB | FAW | CEW | ECB | FAW |
|---|---|---|---|---|---|---|---|---|
| Cry 34/35Ab1 120 ng/cm² | negative | 0.083 | 0 | 0 | 0 | 0 | 0 | 0 |
| BSA 100 µg/cm² | negative | 0.917 | 0 | 0 | 0 | 0 | 0 | 0 |
| Cry1Ac 30 ng/cm² | positive | 1.0 | 1.0 | 1.0 | 0 | 1.0 | 1.0 | 0.333 |
| Cry1Fa 120 ng/cm² | positive | 1.0 | 0 | 1.0 | 1.0 | 0 | 1.0 | 1.0 |
| PBS | negative | 0.167 | 0 | 0 | 0.167 | 0 | 0 | 0 |
| 20 mM Na Citrate, pH 3.5 | negative | 0.250 | 0 | 0 | 0.167 | 0 | 0 | 0 |

The foregoing describes a method of applying an isolated IRDIG17912 insecticidal polypeptide and controlling a coleopteran and/or lepidopteran pest population in accordance with the invention.

TABLE 8

Dose response of TcdA, Cry34/35Ab1, and IRDIG17912 full length

| Dose response parameters | TcdA | | Cry34/35Ab1 | | IRDIG17912 | |
|---|---|---|---|---|---|---|
| # Experiment Dates | 2 | | 2 | | 1 | |
| # test larvae | 479 | | 413 | | 214 | |
|  | Estimate | SE | Estimate | SE | Estimate | SE |
| Mortality + Moribund | | | | | | |
| LC50 | 4.5 | 3.6-5.7 | 69.3 | 42.8-112.2 | 29.7 | 21.6-40.7 |
| LC90 | 16.1 | 11.1-23.3 | out of range | | 173.3* | 70.6-425.5* |
| Slope | 1.01 | 0.14 | 0.49 | 0.07 | 0.73 | 0.16 |
| Normalized live weight, pooled (GI) | | | | | | |
| EC50 | 1.7 | 0.7-4.3 | 1.8 | 1.2-2.6 | 8.4 | 6.8-10.4 |
| EC90 | 16.7 | 3.5-79.1 | 14.2 | 6.9-29.4 | 33.4 | 23.2-48.0 |
| Slope | 0.97 | 0.44 | 1.06 | 0.19 | 1.59 | 0.21 |

*Values have been extrapolated beyond the tested rate range

Example 6

Production of IRDIG17912 Insecticidal Toxins in Dicot Plants

*Arabidopsis* Transformation.

*Arabidopsis thaliana* Col-01 is transformed using the floral dip method (Weigel and Glazebrook, 2002). The selected *Agrobacterium* colony is used to inoculate 1 mL to 15 mL cultures of YEP broth containing appropriate antibiotics for selection. The culture is incubated overnight at 28° C. with constant agitation at 220 rpm. Each culture is used to inoculate two 500 mL cultures of YEP broth containing appropriate antibiotics for selection and the new cultures are incubated overnight at 28° C. with constant agitation. The cells are pelleted at approximately 8700×g for 10 minutes at room temperature, and the resulting supernatant is discarded. The cell pellet is gently resuspended in 500 mL of infiltration media containing: ½× Murashige and Skoog salts (Sigma-Aldrich)/Gamborg's B5 vitamins (Gold Bio-Technology, St. Louis, Mo.), 10% (w/v) sucrose, 0.044 µM benzylaminopurine (10 µL/liter of 1 mg/mL stock in DMSO) and 300 µL/liter Silwet L-77. Plants approximately 1 month old are dipped into the media for 15 seconds, with care taken to assure submergence of the newest inflorescence. The plants are then laid on their sides and covered (transparent or opaque) for 24 hours, washed with water, and placed upright. The plants are grown at 22° C., with a 16-hour light/8-hour dark photoperiod. Approximately 4 weeks after dipping, the seeds are harvested.

*Arabidopsis* Growth and Selection.

Freshly harvested T1 seed is allowed to dry for at least 7 days at room temperature in the presence of desiccant. Seed is suspended in a 0.1% agar/water (Sigma-Aldrich) solution and then stratified at 4° C. for 2 days. To prepare for planting, Sunshine Mix LP5 (Sun Gro Horticulture Inc., Bellevue, Wash.) in 10.5 inch×21 inch germination trays (T.O. Plastics Inc., Clearwater, Minn.) is covered with fine vermiculite, sub-irrigated with Hoagland's solution (Hoagland and Arnon, 1950) until wet, then allowed to drain for 24 hours. Stratified seed is sown onto the vermiculite and covered with humidity domes (KORD Products, Bramalea, Ontario, Canada) for 7 days. Seeds are germinated and plants are grown in a Conviron™ growth chamber (Models CMP4030 or CMP3244; Controlled Environments Limited, Winnipeg, Manitoba, Canada) under long day conditions (16 hours light/8 hours dark) at a light intensity of 120-150 µmol/m² sec under constant temperature (22° C.) and humidity (40-50%). Plants are initially watered with Hoagland's solution and subsequently with deionized water to keep the soil moist but not wet.

The domes are removed 5-6 days post sowing and plants are sprayed with a chemical selection agent to kill plants germinated from nontransformed seeds. For example, if the plant expressible selectable marker gene provided by the binary plant transformation vector is a pat or bar gene (Wehrmann et al., 1996), transformed plants may be selected by spraying with a 1000× solution of Finale (5.78% glufosinate ammonium, Farnam Companies Inc., Phoenix, Ariz.). Two subsequent sprays are performed at 5-7 day intervals. Survivors (plants actively growing) are identified 7-10 days after the final spraying and transplanted into pots prepared with Sunshine Mix LP5. Transplanted plants are covered with a humidity dome for 3-4 days and placed in a Conviron™ growth chamber under the above-mentioned growth conditions.

Those skilled in the art of dicot plant transformation will understand that other methods of selection of transformed plants are available when other plant expressible selectable marker genes (e.g., herbicide tolerance genes) are used.

Insect Bioassays of Transgenic *Arabidopsis*.

Transgenic *Arabidopsis* lines expressing IRDIG17912 insecticidal toxin proteins are demonstrated to be active against sensitive insect species in artificial diet overlay assays. Protein extracted from transgenic and non-transgenic *Arabidopsis* lines is quantified by appropriate methods and sample volumes are adjusted to normalize protein concentration. Bioassays are conducted on artificial diet as described above. Non-transgenic *Arabidopsis* and/or buffer and water are included in assays as background check treatments.

The foregoing provides methods for making and using transgenic plants comprising IRDIG17912 insecticidal toxin polypeptides according to the invention.

Example 7

Production of IRDIG17912 Insecticidal Proteins in Monocot Plants

*Agrobacterium*-Mediated Transformation of Maize.

Transgenic maize cells, tissues, and plants that produce one or more insecticidal proteins through expression of a chimeric gene stably-integrated into the plant genome were produced following *Agrobacterium*-mediated transformation. Maize transformation methods employing superbinary or binary transformation vectors are known in the art, as described, for example, in U.S. Pat. No. 8,304,604, which is herein incorporated by reference in its entirety. Transformed tissues were selected by their ability to grow on Haloxyfop-containing medium and were screened for protein production, as appropriate. Portions of such transformed tissue cultures were presented to insect larvae for bioassay, essentially as described in EXAMPLE 5.

*Agrobacterium* Culture Initiation.

Glycerol stocks of the project vectors in the host *Agrobacterium tumefaciens* strain DAt13192 (RecA minus ternary strain) were obtained from the DAS Recombinant Culture Collection (RCC). *Agrobacterium* cultures were streaked from glycerol stocks onto AB minimal medium and incubated at 20° C. in the dark for 3 days. *Agrobacterium* cultures were then streaked onto a plate of YEP medium and incubated at 20° C. in the dark for 1 day.

On the day of an experiment, a mixture of Inoculation medium and acetosyringone was prepared in a volume appropriate to the number of constructs in the experiment. Inoculation medium was pipetted into a sterile, disposable, 250 ml flask. A 1 M stock solution of acetosyringone in 100% dimethyl sulfoxide was added to the flask containing inoculation medium in a volume appropriate to make a final acetosyringone concentration of 200 µM.

For each construct, 1-2 loops of *Agrobacterium* from the YEP plate were suspended in 15 mL of the inoculation medium/acetosyringone mixture inside a sterile, disposable, 50 mL centrifuge tube and the optical density of the solution at 600 nm (O.D.$_{600}$) was measured in a spectrophotometer. The suspension was then diluted down to 0.25-0.35 O.D.$_{600}$ using additional Inoculation medium/acetosyringone mixture. The tube of *Agrobacterium* suspension was then placed horizontally on a platform shaker set at about 75 rpm at room temperature for between 1 and 4 hours before use.

Ear Sterilization and Embryo Isolation.

Ears from *Zea mays* cultivar B104 were produced in greenhouse facilities and harvested 10-12 days post pollination. Harvested ears were de-husked and surface-sterilized by immersion in a 20% solution of commercial bleach (Ultra Clorox® Germicidal Bleach, 6.15% sodium hypochlorite) and two drops of soap, for 20 minutes, followed by three rinses in sterile, deionized water inside a laminar flow hood. Immature zygotic embryos (1.8-2.2 mm long) were aseptically excised from each ear and distributed into one or more micro-centrifuge tubes containing 2.0 mL of *Agrobacterium* suspension into which 2 µl of 10% Break-Thru® 5233 surfactant had been added.

*Agrobacterium* Co-Cultivation.

Upon completion of the embryo isolation activity the tube of embryos was closed and placed on a rocker platform for 5 minutes. The contents of the tube were then poured out onto a plate of co-cultivation medium and the liquid *Agrobacterium* suspension was removed with a sterile, disposable, transfer pipette and the embryos were oriented with the scutellum facing up using a microscope. The plate was then closed, sealed with 3M Micropore tape, and placed in an incubator at 25° C. with 24 hours/day light at approximately 60 µmol $m^{-2}$ $s^{-1}$ photosynthetically active radiation (PAR).

Callus Selection and Regeneration of Transgenic Events.

Following the co-cultivation period, embryos were transferred to Resting medium. No more than 36 embryos were moved to each plate. The plates were incubated at 27° C. with 24 hours/day light at approximately 50 µmol $m^{-2}$ $s^{-1}$ PAR for 7-10 days. Callused embryos were then transferred onto Selection I medium. No more than 18 callused embryos were moved to each plate of Selection I. The plates were incubated at 27° C. with 24 hours/day light at approximately 50 µmol $m^{-2}$ $s^{-1}$ PAR for 7 days. Callused embryos were then transferred to Selection II medium. No more than 12 callused embryos were moved to each plate of Selection II. The plates were incubated at 27° C. with 24 hours/day light at approximately 50 µmol $m^{-2}$ $s^{-1}$ PAR for 14 days.

At this stage resistant calli were moved to Pre-Regeneration medium. No more than 9 calli were moved to each plate of Pre-Regeneration. The plates were at 27° C. with 24 hours/day light at approximately 50 µmol $m^{-2}$ $s^{-1}$ PAR for 7 days. Regenerating calli were then transferred to Regeneration medium in Phytatrays™ (SIGMA-ALDRICH). and incubated at 28° C. with 16 hours light/8 hours dark per day at approximately 150 µmol $m^{-2}$ $s^{-1}$ PAR for 7-14 days or until shoots develop. No more than 5 calli were placed in each Phytatray™. Small shoots with primary roots were then isolated and transferred to Shoot/Root medium. Rooted plantlets about 6 cm or taller were transplanted into soil and moved out to a growth chamber for hardening off.

Transformed plant shoots selected by their ability to grow on medium containing Haloxyfop were transplanted from PHYTATRAYS™ to small pots filled with growing medium (PROMIX BX; PREMIER TECH HORTICULTURE), covered with cups or HUMI-DOMES (ARCO PLASTICS), and then hardened-off in a CONVIRON growth chamber (27° C. day/24° C. night, 16-hour photoperiod, 50-70% RH, 200 µmol $m^{-2}$ $s^{-1}$ PAR). In some instances, putative transgenic plantlets were analyzed for transgene relative copy number by quantitative real-time PCR assays using primers designed to detect the herbicide tolerance gene integrated into the maize genome. Further, RNA qPCR assays were used to detect the presence of the linker sequence in expressed dsRNAs of putative transformants. Selected transformed plantlets were then moved into a greenhouse for further growth and testing.

Transfer and Establishment of to Plants in the Greenhouse for Bioassay and Seed Production.

Plants were transplanted from Phytatrays™ to small pots (T. O. Plastics, 3.5" SVD, 700022C) filled with growing media (Premier Tech Horticulture, ProMix BX, 0581 P) and covered with humidomes to acclimate the plants. They were placed in a Conviron growth chamber (28° C./24° C., 16-hour photoperiod, 50-70% RH, 200 µmol $m^{-2}$ $s^{-1}$ PAR) until they reached V3-V4 stage. This aided in acclimating the plants to soil and harsher temperatures. Plants were then moved to the greenhouse (Light Exposure Type: Photo or Assimilation; High Light Limit: 1200 µmol $m^{-2}$ $s^{-1}$ PAR; 16-hour day length; 27° C. day/24° C. night) and transplanted from the small pots to 5 gallon pots. Approximately 1-2 weeks after transplanting to larger pots plants were sampled for bioassay. One plant per event was bioassayed.

Plants to be used for insect bioassays were transplanted from small pots to TINUS™ 350-4 ROOTRAINERS® (SPENCER-LEMAIRE INDUSTRIES, Acheson, Alberta, Canada) (one plant per event per ROOTRAINER®). Approximately four days after transplanting to ROOTRAINERS®, plants were infested for bioassay.

Plants of the $T_1$ generation were obtained by pollinating the silks of $T_0$ transgenic plants with pollen collected from plants of non-transgenic elite inbred line B104 or other appropriate pollen donors, and planting the resultant seeds. Reciprocal crosses were performed when possible.

The foregoing provides methods for making and regenerating transgenic plants comprising IRDIG17912 insecticidal toxin polypeptides according to the invention.

Example 8

Bioassay of Transgenic Maize

Bioactivity of the IRDIG17912 insecticidal toxins produced in plant cells is demonstrated by conventional bioassay methods (see, for example Huang et al., 2006). In one assay of efficacy, various plant tissues or tissue pieces derived from a plant producing a IRDIG17912 insecticidal toxin are fed to target insects in a controlled feeding environment. In another bioactivity assay, protein extracts are prepared from various plant tissues derived from the plant producing the IRDIG17912 insecticidal toxin and the extracted proteins are incorporated into artificial diet bioassays. The results of each feeding assay are compared to similarly conducted bioassays that employ appropriate control tissues from host plants that do not produce a IRDIG17912 insecticidal toxin, or to other control samples.

Example 9

Transgenic *Glycine max* Comprising IRDIG17912

Ten to 20 transgenic $T_0$ *Glycine max* plants harboring expression vectors for nucleic acids comprising IRDIG17912 are generated by *Agrobacterium*-mediated transformation. Mature soybean (*Glycine max*) seeds are sterilized overnight with chlorine gas for sixteen hours. Following sterilization with chlorine gas, the seeds are placed in an open container in a LAMINAR™ flow hood to dispel the chlorine gas. Next, the sterilized seeds are imbibed with sterile $H_2O$ for sixteen hours in the dark using a black box at 24° C.

Preparation of Split-Seed Soybeans.

The split soybean seed comprising a portion of an embryonic axis protocol required preparation of soybean seed material which is cut longitudinally, using a #10 blade affixed to a scalpel, along the hilum of the seed to separate and remove the seed coat, and to split the seed into two cotyledon sections. Careful attention is made to partially remove the embryonic axis, wherein about ½-⅓ of the embryo axis remains attached to the nodal end of the cotyledon.

Inoculation.

The split soybean seeds comprising a partial portion of the embryonic axis are then immersed for about 30 minutes in a solution of *Agrobacterium tumefaciens* (e.g., strain EHA 101 or EHA 105) containing binary plasmid comprising IRDIG17912. The *Agrobacterium tumefaciens* solution is diluted to a final concentration of λ=0.6 $OD_{650}$ before immersing the cotyledons comprising the embryo axis.

Co-Cultivation.

Following inoculation, the split soybean seed is allowed to co-cultivate with the *Agrobacterium tumefaciens* strain for 5 days on co-cultivation medium (Wang, Kan. *Agrobacterium* Protocols. 2. 1. New Jersey: Humana Press, 2006. Print.) in a Petri dish covered with a piece of filter paper.

Shoot Induction.

After 5 days of co-cultivation, the split soybean seeds are washed in liquid Shoot Induction (SI) media consisting of B5 salts, B5 vitamins, 28 mg/L Ferrous, 38 mg/L $Na_2EDTA$, 30 g/L sucrose, 0.6 g/L MES, 1.11 mg/L BAP, 100 mg/L TIMENTIN™, 200 mg/L cefotaxime, and 50 mg/L vancomycin (pH 5.7). The split soybean seeds are then cultured on Shoot Induction I (SI I) medium consisting of B5 salts, B5 vitamins, 7 g/L Noble agar, 28 mg/L Ferrous, 38 mg/L $Na_2EDTA$, 30 g/L sucrose, 0.6 g/L MES, 1.11 mg/L BAP, 50 mg/L TIMENTIN™, 200 mg/L cefotaxime, 50 mg/L vancomycin (pH 5.7), with the flat side of the cotyledon facing up and the nodal end of the cotyledon imbedded into the medium. After 2 weeks of culture, the explants from the transformed split soybean seed are transferred to the Shoot Induction II (SI II) medium containing SI I medium supplemented with 6 mg/L glufosinate (LIBERTY®).

Shoot Elongation.

After 2 weeks of culture on SI II medium, the cotyledons are removed from the explants and a flush shoot pad containing the embryonic axis are excised by making a cut at the base of the cotyledon. The isolated shoot pad from the cotyledon is transferred to Shoot Elongation (SE) medium. The SE medium consists of MS salts, 28 mg/L Ferrous, 38 mg/L $Na_2EDTA$, 30 g/L sucrose and 0.6 g/L MES, 50 mg/L asparagine, 100 mg/L L-pyroglutamic acid, 0.1 mg/L IAA, 0.5 mg/L GA3, 1 mg/L zeatin riboside, 50 mg/L TIMENTIN™, 200 mg/L cefotaxime, 50 mg/L vancomycin, 6 mg/L glufosinate, 7 g/L Noble agar, (pH 5.7). The cultures are transferred to fresh SE medium every 2 weeks. The cultures are grown in a CONVIRON™ growth chamber at 24° C. with an 18 h photoperiod at a light intensity of 80-90 μmol/m² sec.

Rooting.

Elongated shoots which developed from the cotyledon shoot pad are isolated by cutting the elongated shoot at the base of the cotyledon shoot pad, and dipping the elongated shoot in 1 mg/L IBA (Indole 3-butyric acid) for 1-3 minutes to promote rooting. Next, the elongated shoots are transferred to rooting medium (MS salts, B5 vitamins, 28 mg/L Ferrous, 38 mg/L $Na_2EDTA$, 20 g/L sucrose and 0.59 g/L MES, 50 mg/L asparagine, 100 mg/L L-pyroglutamic acid 7 g/L Noble agar, pH 5.6) in phyta trays.

Cultivation.

Following culture in a CONVIRON™ growth chamber at 24° C., 18 h photoperiod, for 1-2 weeks, the shoots which have developed roots are transferred to a soil mix in a covered sundae cup and placed in a CONVIRON™ growth chamber (models CMP4030 and CMP3244, Controlled Environments Limited, Winnipeg, Manitoba, Canada) under long day conditions (16 hours light/8 hours dark) at a light intensity of 120-150 μmol/m² sec under constant temperature (22° C.) and humidity (40-50%) for acclimatization of plantlets. The rooted plantlets are acclimated in sundae cups for several weeks before they are transferred to the greenhouse for further acclimatization and establishment of robust transgenic soybean plants.

Development and morphological characteristics of transgenic lines are compared with nontransformed plants. Plant root, shoot, foliage and reproduction characteristics are compared. There are no observable difference in root length and growth patterns of transgenic and nontransformed plants. Plant shoot characteristics such as height, leaf numbers and sizes, time of flowering, floral size and appearance are similar. In general, there are no observable morphological differences between transgenic lines and those without expression of DIG proteins when cultured in vitro and in soil in the glasshouse.

The foregoing provides methods for making and selecting transgenic dicot plants (soybeans) comprising IRDIG17912 insecticidal toxin polypeptides according to the invention.

The invention claimed is:

1. An engineered chimeric insecticidal toxin selected from the group consisting of SEQ ID NO: 8, SEQ ID NO: 10, SEQ ID NO: 12, SEQ ID NO: 14, SEQ ID NO: 16, and a toxin having at least 95% sequence identity with SEQ ID NO: 8, SEQ ID NO: 10, SEQ ID NO: 12, SEQ ID NO: 14, or SEQ ID NO: 16.

2. A DNA sequence encoding an engineered chimeric insecticidal toxin of claim 1.

3. A nucleic acid construct comprising a nucleic acid sequence encoding an IRDIG17912 insecticidal toxin of SEQ ID NO: 2 or SEQ ID NO: 4, or a toxin having at least 95% sequence identity with SEQ ID NO: 2 or SEQ ID NO: 4, operably linked to a heterologous promoter capable of driving expression in a plant.

4. A nucleic acid construct comprising the DNA of claim 2, operably linked to a heterologous-promoter capable of driving expression in a plant.

5. A transgenic plant or plant part comprising the toxin of claim 1.

6. A transgenic plant or plant part comprising the nucleic acid construct of claim 3.

7. A transgenic plant or plant part comprising the nucleic acid construct of claim 4.

8. A method for controlling a western corn rootworm pest population comprising contacting members of said western corn rootworm pest population with the transgenic plant or plant part of claim 6.

9. A method for controlling a western corn rootworm pest population comprising contacting members of said western corn rootworm pest population with the transgenic plant or plant part of claim 7.

10. A method for controlling a western corn rootworm pest population comprising contacting members of said western corn rootworm pest population with a pesticidally effective amount of the insecticidal toxin of claim 1.

11. A *Pseudomonas fluorescens* host strain engineered to express a DNA encoding an IRDIG17912 insecticidal toxin of SEQ ID NO: 2 or SEQ ID NO: 4, or a toxin having at least 95% sequence identity with SEQ ID NO: 2 or SEQ ID NO: 4.

* * * * *

SEQUENCE LISTING

```
<160> NUMBER OF SEQ ID NOS: 16

<210> SEQ ID NO 1
<211> LENGTH: 963
<212> TYPE: DNA
<213> ORGANISM: Bacillus thuringiensis

<400> SEQUENCE: 1
atgtacacaa gtatttataa attagaggaa aattctgagg aaaatcgtct ttcaaaggaa      60
cgatcgtttt tgcttaaaaa ctattcaatt aaaaaggaga gattttatat gactaccaaa     120
aatttaagtg atttagaaat ggaaataagt aataatcaac aacaactaaa acgtttaatt     180
gctccagctt tccgacatat tgtattaaaa gttccagcta gcgaagaaag taattataaa     240
gaaatcttcc aggtagagcc acggtatatc gctcaagctc ttcgtttagc taatgctttc     300
caaggcgctc tagatccaac tgatttaaat tttaatttcg aaaaagcatt gcaaatcgca     360
```

-continued

```
caacatattc cgaattcagc aatcgttaag actcttaacc aaaatgtagt acagcaaact    420
gttgaaatat cagctatgat cagtcagcta aagcaaatta ttaaagatgt tttaggactt    480
gttatttcta gtcctaattt ttggaattca gtagaggctg ctgttactaa cacgtttaca    540
aatctaagta ctcaagaaga tggagcttgg attttttgga agagttcatc ttcttcaaac    600
acaagttatt attataacat tctatttct attcaaaatg cagaaacagg tgcagtgatg    660
gcagtattac ctatagcatt tgagatttca gttaaccttg aaaaacaaaa agtattattt    720
cttacaatta gagacagcgc acgatatgag gttaaattga agctattac tttagttcaa     780
gctttggact ctttcaatgc accaattaca gatgtattta cgttcataa ctatggtcca     840
tatccaccaa taaattcaaa cgtaaatgat cttattattc ggaatttgat gttaaataac    900
acaaattcta atgattttat tcttcaggat ttaatagata atcaacataa tgacaaaaaa    960
gag                                                                 963
```

<210> SEQ ID NO 2
<211> LENGTH: 321
<212> TYPE: PRT
<213> ORGANISM: Bacillus thuringiensis
<400> SEQUENCE: 2

```
Met Tyr Thr Ser Ile Tyr Lys Leu Glu Glu Asn Ser Glu Glu Asn Arg
1               5                   10                  15

Leu Ser Lys Glu Arg Ser Phe Leu Leu Lys Asn Tyr Ser Ile Lys Lys
            20                  25                  30

Glu Arg Phe Tyr Met Thr Thr Lys Asn Leu Ser Asp Leu Glu Met Glu
        35                  40                  45

Ile Ser Asn Asn Gln Gln Gln Leu Lys Arg Leu Ile Ala Pro Ala Phe
    50                  55                  60

Arg His Ile Val Leu Lys Val Pro Ala Ser Glu Ser Asn Tyr Lys
65                  70                  75                  80

Glu Ile Phe Gln Val Glu Pro Arg Tyr Ile Ala Gln Ala Leu Arg Leu
                85                  90                  95

Ala Asn Ala Phe Gln Gly Ala Leu Asp Pro Thr Asp Leu Asn Phe Asn
            100                 105                 110

Phe Glu Lys Ala Leu Gln Ile Ala Gln His Ile Pro Asn Ser Ala Ile
        115                 120                 125

Val Lys Thr Leu Asn Gln Asn Val Gln Gln Thr Val Glu Ile Ser
    130                 135                 140

Ala Met Ile Ser Gln Leu Lys Gln Ile Ile Lys Asp Val Leu Gly Leu
145                 150                 155                 160

Val Ile Ser Ser Pro Asn Phe Trp Asn Ser Val Glu Ala Ala Val Thr
                165                 170                 175

Asn Thr Phe Thr Asn Leu Ser Thr Gln Glu Asp Gly Ala Trp Ile Phe
            180                 185                 190

Trp Lys Ser Ser Ser Ser Ser Asn Thr Ser Tyr Tyr Asn Ile Leu
        195                 200                 205

Phe Ser Ile Gln Asn Ala Glu Thr Gly Ala Val Met Ala Val Leu Pro
    210                 215                 220

Ile Ala Phe Glu Ile Ser Val Asn Leu Glu Lys Gln Lys Val Leu Phe
225                 230                 235                 240

Leu Thr Ile Arg Asp Ser Ala Arg Tyr Glu Val Lys Leu Lys Ala Ile
                245                 250                 255
```

Thr Leu Val Gln Ala Leu Asp Ser Phe Asn Ala Pro Ile Thr Asp Val
            260                 265                 270

Phe Asn Val His Asn Tyr Gly Pro Tyr Pro Ile Asn Ser Asn Val
        275                 280                 285

Asn Asp Leu Ile Ile Arg Asn Leu Met Leu Asn Asn Thr Asn Ser Asn
    290                 295                 300

Asp Phe Ile Leu Gln Asp Leu Ile Asp Asn Gln His Asn Asp Lys Lys
305                 310                 315                 320

Glu

<210> SEQ ID NO 3
<211> LENGTH: 855
<212> TYPE: DNA
<213> ORGANISM: Bacillus thuringiensis

<400> SEQUENCE: 3
atgaccacca agaacctgtc cgacctggag atggagatca gcaataatca acagcagctg    60
aagaggctga tcgcaccggc ctttaggcac atcgtattaa aggtgccagc cagcgaggag   120
agcaactaca aggaaatctt ccaagtggag cctcgctaca tcgcccaagc gctgaggctg   180
gcgaacgcct tccaaggcgc actggacccg accgacctga acttcaactt cgagaaagca   240
ttgcagatcg ctcagcacat cccgaacagc gccatcgtga aaccctgaa ccaaaacgtg   300 gtgcagcaga ccgtggagat ccgccatg atcagccagc tgaagcagat cattaaagac   360
gtgctgggcc tggtgatcag ctccccgaac ttctggaact ccgtggaggc tgccgtgacc   420
aacaccttca ccaacctgtc cacccaagag acggagcgt ggatcttctg gaagtccagc   480
tcctccagca acaccagcta ctactacaac atcctgttca gcatccagaa cgcggagacc   540
ggagccgtga tggcggtgct gccgattgcg ttcgagattt ccgtgaacct ggagaagcag   600
aaggtgctgt tcctgaccat aagggactcc gcgagatacg aggtgaagct gaaggctatc   660
accctggtgc aagcgctgga ctccttcaac gcaccgatca ccgacgtgtt caacgtccac   720
aactacggtc cgtacccacc aataaacagc aacgtgaacg acctgatcat ccggaacctg   780
atgctgaaca acaccaactc aaacgacttc atcctccaag acctgatcga caatcaacac   840
aacgacaaga aggag                                                    855

<210> SEQ ID NO 4
<211> LENGTH: 285
<212> TYPE: PRT
<213> ORGANISM: Bacillus thuringiensis

<400> SEQUENCE: 4

Met Thr Thr Lys Asn Leu Ser Asp Leu Glu Met Glu Ile Ser Asn Asn
1               5                   10                  15

Gln Gln Gln Leu Lys Arg Leu Ile Ala Pro Ala Phe Arg His Ile Val
            20                  25                  30

Leu Lys Val Pro Ala Ser Glu Glu Ser Asn Tyr Lys Glu Ile Phe Gln
        35                  40                  45

Val Glu Pro Arg Tyr Ile Ala Gln Ala Leu Arg Leu Ala Asn Ala Phe
    50                  55                  60

Gln Gly Ala Leu Asp Pro Thr Asp Leu Asn Phe Asn Phe Glu Lys Ala
65                  70                  75                  80

Leu Gln Ile Ala Gln His Ile Pro Asn Ser Ala Ile Val Lys Thr Leu
            85                  90                  95

Asn Gln Asn Val Val Gln Gln Thr Val Glu Ile Ser Ala Met Ile Ser

```
             100                 105                 110
Gln Leu Lys Gln Ile Ile Lys Asp Val Leu Gly Leu Val Ile Ser Ser
            115                 120                 125

Pro Asn Phe Trp Asn Ser Val Glu Ala Ala Val Thr Asn Thr Phe Thr
130                 135                 140

Asn Leu Ser Thr Gln Glu Asp Gly Ala Trp Ile Phe Trp Lys Ser Ser
145                 150                 155                 160

Ser Ser Ser Asn Thr Ser Tyr Tyr Tyr Asn Ile Leu Phe Ser Ile Gln
                165                 170                 175

Asn Ala Glu Thr Gly Ala Val Met Ala Val Leu Pro Ile Ala Phe Glu
            180                 185                 190

Ile Ser Val Asn Leu Glu Lys Gln Lys Val Leu Phe Leu Thr Ile Arg
        195                 200                 205

Asp Ser Ala Arg Tyr Glu Val Lys Leu Lys Ala Ile Thr Leu Val Gln
    210                 215                 220

Ala Leu Asp Ser Phe Asn Ala Pro Ile Thr Asp Val Phe Asn Val His
225                 230                 235                 240

Asn Tyr Gly Pro Tyr Pro Pro Ile Asn Ser Asn Val Asn Asp Leu Ile
                245                 250                 255

Ile Arg Asn Leu Met Leu Asn Asn Thr Asn Ser Asn Asp Phe Ile Leu
            260                 265                 270

Gln Asp Leu Ile Asp Asn Gln His Asn Asp Lys Lys Glu
        275                 280                 285

<210> SEQ ID NO 5
<211> LENGTH: 963
<212> TYPE: DNA
<213> ORGANISM: Artificial Sequence
<220> FEATURE:
<223> OTHER INFORMATION: synthesized full length coding region

<400> SEQUENCE: 5
atgtacacct ccatctataa gctggaggag aactccgagg agaacagact gtccaaggag      60
aggagcttcc tgctgaagaa ctactcaatt aaaaaggaga gattctacat gaccaccaag     120
aacctgtccg acctggagat ggagatcagc aataatcaac agcagctgaa gaggctgatc     180
gcaccggcct ttaggcacat cgtattaaag gtgccagcca gcgaggagag caactacaag     240
gaaatcttcc aagtggagcc tcgctacatc gcccaagcgc tgaggctggc gaacgccttc     300
caaggcgcac tggacccgac cgacctgaac ttcaacttcg agaaagcatt gcagatcgct     360
cagcacatcc cgaacagcgc catcgtgaaa accctgaacc aaaacgtggt gcagcagacc     420
gtggagatat ccgccatgat cagccagctg aagcagatca ttaaagacgt gctgggcctg     480
gtgatcagct cccgaacttt ctggaactcc gtggaggctg ccgtgaccaa caccttcacc     540
aacctgtcca cccaagagga cggagcgtgg atcttctgga agtccagctc ctccagcaac     600
accagctact actacaacat cctgttcagc atccagaacg cggagaccgg agccgtgatg     660
gcggtgctgc cgattgcgtt cgagatttcc gtgaacctgg agaagcagaa ggtgctgttc     720
ctgaccataa gggactccgc gagatacgag gtgaagctga aggctatcac cctggtgcaa     780
gcgctggact ccttcaacgc accgatcacc gacgtgttca acgtccacaa ctacggtccg     840
tacccaccaa taaacagcaa cgtgaacgac ctgatcatcc ggaacctgat gctgaacaac     900
accaactcaa acgacttcat cctccaagac ctgatcgaca tcaacacaa cgacaagaag     960 gag                                                                  963
```

```
<210> SEQ ID NO 6
<211> LENGTH: 855
<212> TYPE: DNA
<213> ORGANISM: Artificial Sequence
<220> FEATURE:
<223> OTHER INFORMATION: synthesized coding region

<400> SEQUENCE: 6
atgaccacca agaacctgtc cgacctggag atggagatca gcaataatca acagcagctg      60
aagaggctga tcgcaccggc ctttaggcac atcgtattaa aggtgccagc cagcgaggag     120
agcaactaca aggaaatctt ccaagtggag cctcgctaca tcgcccaagc gctgaggctg     180
gcgaacgcct tccaaggcgc actggacccg accgacctga acttcaactt cgagaaagca     240
ttgcagatcg ctcagcacat cccgaacagc gccatcgtga aaaccctgaa ccaaaacgtg     300
gtgcagcaga ccgtggagat atccgccatg atcagccagc tgaagcagat cattaaagac     360
gtgctgggcc tggtgatcag ctccccgaac ttctggaact ccgtggaggc tgccgtgacc     420
aacaccttca ccaacctgtc cacccaagag gacggagcgt ggatcttctg gaagtccagc     480
tcctccagca acaccagcta ctactacaac atcctgttca gcatccagaa cgcggagacc     540
ggagccgtga tggcggtgct gccgattgcg ttcgagattt ccgtgaacct ggagaagcag     600
aaggtgctgt cctgaccat aagggactcc gcgagatacg aggtgaagct gaaggctatc     660
accctggtgc aagcgctgga ctccttcaac gcaccgatca ccgacgtgtt caacgtccac     720
aactacggtc cgtacccacc aataaacagc aacgtgaacg acctgatcat ccggaacctg     780
atgctgaaca acaccaactc aaacgacttc atcctccaag acctgatcga caatcaacac     840
aacgacaaga aggag                                                      855

<210> SEQ ID NO 7
<211> LENGTH: 1176
<212> TYPE: DNA
<213> ORGANISM: Artificial Sequence
<220> FEATURE:
<223> OTHER INFORMATION: synthesized coding region

<400> SEQUENCE: 7
atgttggctc gccaaggagg atcactgaga gcctctcagt gtaacgctgg cctcgcgaga      60
cgcgtggagg tgggagcgtt ggttgttccg agacccataa gcgtcaacga cgtggttccc     120
catgtctatt cggctcctct gagcgtcgcg aggaggtcgt gctccaagtc atccatccgc     180
tcgactcgca gacttcagac aaccgtctgc tccatgtaca cctccatcta taagctggag     240
gagaactccg aggagaacag actgtccaag gagaggagct tcctgctgaa gaactactca     300
attaaaaagg agagattcta catgaccacc aagaacctgt ccgacctgga gatggagatc     360
agcaataatc aacagcagct gaagaggctg atcgcaccgg cctttaggca catcgtatta     420
aaggtgccag ccagcgagga gagcaactac aaggaaatct tccaagtgga gcctcgctac     480
atcgcccaag cgctgaggct ggcgaacgcc ttccaaggcg cactggaccc gaccgacctg     540
aacttcaact tcgagaaagc attgcagatc gctcagcaca tcccgaacag cgccatcgtg     600
aaaaccctga ccaaaacgt ggtgcagcag accgtggaga tatccgccat gatcagccag     660
ctgaagcaga tcattaaaga cgtgctgggc ctggtgatca gctccccgaa cttctggaac     720
tccgtggagg ctgccgtgac caacaccttc accaacctgt ccacccaaga ggacggagcg     780
tggatcttct ggaagtccag ctcctccagc aacaccagct actactacaa catcctgttc     840
agcatccaga acgcggagac cggagccgtg atggcggtgc tgccgattgc gttcgagatt     900
```

-continued

```
tccgtgaacc tggagaagca gaaggtgctg ttcctgacca taagggactc cgcgagatac    960
gaggtgaagc tgaaggctat caccctggtg caagcgctgg actccttcaa cgcaccgatc   1020
accgacgtgt tcaacgtcca caactacggt ccgtacccac caataaacag caacgtgaac   1080
gacctgatca tccggaacct gatgctgaac aacaccaact caaacgactt catcctccaa   1140
gacctgatcg acaatcaaca aacgacaag aaggag                              1176
```

<210> SEQ ID NO 8
<211> LENGTH: 392
<212> TYPE: PRT
<213> ORGANISM: Artificial Sequence
<220> FEATURE:
<223> OTHER INFORMATION: translated from synthesized coding region

<400> SEQUENCE: 8

```
Met Leu Ala Arg Gln Gly Gly Ser Leu Arg Ala Ser Gln Cys Asn Ala
1               5                   10                  15

Gly Leu Ala Arg Arg Val Glu Val Gly Ala Leu Val Val Pro Arg Pro
            20                  25                  30

Ile Ser Val Asn Asp Val Val Pro His Val Tyr Ser Ala Pro Leu Ser
        35                  40                  45

Val Ala Arg Arg Ser Cys Ser Lys Ser Ser Ile Arg Ser Thr Arg Arg
    50                  55                  60

Leu Gln Thr Thr Val Cys Ser Met Tyr Thr Ser Ile Tyr Lys Leu Glu
65                  70                  75                  80

Glu Asn Ser Glu Glu Asn Arg Leu Ser Lys Glu Arg Ser Phe Leu Leu
                85                  90                  95

Lys Asn Tyr Ser Ile Lys Lys Glu Arg Phe Tyr Met Thr Thr Lys Asn
            100                 105                 110

Leu Ser Asp Leu Glu Met Glu Ile Ser Asn Asn Gln Gln Gln Leu Lys
        115                 120                 125

Arg Leu Ile Ala Pro Ala Phe Arg His Ile Val Leu Lys Val Pro Ala
    130                 135                 140

Ser Glu Glu Ser Asn Tyr Lys Glu Ile Phe Gln Val Glu Pro Arg Tyr
145                 150                 155                 160

Ile Ala Gln Ala Leu Arg Leu Ala Asn Ala Phe Gln Gly Ala Leu Asp
                165                 170                 175

Pro Thr Asp Leu Asn Phe Asn Phe Glu Lys Ala Leu Gln Ile Ala Gln
            180                 185                 190

His Ile Pro Asn Ser Ala Ile Val Lys Thr Leu Asn Gln Asn Val Val
        195                 200                 205

Gln Gln Thr Val Glu Ile Ser Ala Met Ile Ser Gln Leu Lys Gln Ile
    210                 215                 220

Ile Lys Asp Val Leu Gly Leu Val Ile Ser Ser Pro Asn Phe Trp Asn
225                 230                 235                 240

Ser Val Glu Ala Ala Val Thr Asn Thr Phe Thr Asn Leu Ser Thr Gln
                245                 250                 255

Glu Asp Gly Ala Trp Ile Phe Trp Lys Ser Ser Ser Ser Asn Thr
            260                 265                 270

Ser Tyr Tyr Tyr Asn Ile Leu Phe Ser Ile Gln Asn Ala Glu Thr Gly
        275                 280                 285

Ala Val Met Ala Val Leu Pro Ile Ala Phe Glu Ile Ser Val Asn Leu
    290                 295                 300

Glu Lys Gln Lys Val Leu Phe Leu Thr Ile Arg Asp Ser Ala Arg Tyr
```

305                 310                 315                 320
Glu Val Lys Leu Lys Ala Ile Thr Leu Val Gln Ala Leu Asp Ser Phe
              325                 330                 335

Asn Ala Pro Ile Thr Asp Val Phe Asn Val His Asn Tyr Gly Pro Tyr
              340                 345                 350

Pro Pro Ile Asn Ser Asn Val Asn Asp Leu Ile Ile Arg Asn Leu Met
              355                 360                 365

Leu Asn Thr Asn Ser Asn Asp Phe Ile Leu Gln Asp Leu Ile Asp
          370                 375                 380

Asn Gln His Asn Asp Lys Lys Glu
385                 390

<210> SEQ ID NO 9
<211> LENGTH: 1161
<212> TYPE: DNA
<213> ORGANISM: Artificial Sequence
<220> FEATURE:
<223> OTHER INFORMATION: synthesized coding region

<400> SEQUENCE: 9
atggctcaat ctagcagaat ctgccacggt gtgcagaacc catgtgtgat catttccaat      60
ctctccaaat ccaaccagaa caaatctcct ttctcagtca gcctcaagac tcaccagcag     120
cagcgtcgtg cttaccagat atctagctgg ggattgaaga agtcaaacaa cgggtccgtg     180
attcgtccgg ttaaggcaat gtacacctcc atctataagc tggaggagaa ctccgaggag     240
aacagactgt ccaaggagag gagcttcctg ctgaagaact actcaattaa aaaggagaga     300
ttctacatga ccaccaagaa cctgtccgac ctggagatgg agatcagcaa taatcaacag     360
cagctgaaga ggctgatcgc accggccttt aggcacatcg tattaaaggt gccagccagc     420
gaggagagca actacaagga aatcttccaa gtggagcctc gctacatcgc caagcgctg     480 aggctggcga acgccttcca aggcgcactg gacccgaccg acctgaactt caacttcgag     540
aaagcattgc agatcgctca gcacatcccg aacagcgcca tcgtgaaaac cctgaaccaa     600
aacgtggtgc agcagaccgt ggagatatcc gccatgatca gccagctgaa gcagatcatt     660
aaagacgtgc tgggcctggt gatcagctcc ccgaacttct ggaactccgt ggaggctgcc     720
gtgaccaaca ccttcaccaa cctgtccacc aagaggacg gagcgtggat cttctggaag     780
tccagctcct ccagcaacac cagctactac tacaacatcc tgttcagcat ccagaacgcg     840
gagaccggag ccgtgatggc ggtgctgccg attgcgttcg agatttccgt gaacctggag     900
aagcagaagg tgctgttcct gaccataagg gactccgcga gatacgaggt gaagctgaag     960
gctatcaccc tggtgcaagc gctggactcc ttcaacgcac cgatcaccga cgtgttcaac    1020
gtccacaact acggtccgta cccaccaata aacagcaacg tgaacgacct gatcatccgg    1080
aacctgatgc tgaacaacac caactcaaac gacttcatcc tccaagacct gatcgacaat    1140
caacacaacg acaagaagga g                                              1161

<210> SEQ ID NO 10
<211> LENGTH: 387
<212> TYPE: PRT
<213> ORGANISM: Artificial Sequence
<220> FEATURE:
<223> OTHER INFORMATION: translated from synthesized coding region

<400> SEQUENCE: 10

Met Ala Gln Ser Ser Arg Ile Cys His Gly Val Gln Asn Pro Cys Val
1               5                   10                  15

```
Ile Ile Ser Asn Leu Ser Lys Ser Asn Gln Asn Lys Ser Pro Phe Ser
         20                  25                  30

Val Ser Leu Lys Thr His Gln Gln Gln Arg Arg Ala Tyr Gln Ile Ser
             35                  40                  45

Ser Trp Gly Leu Lys Lys Ser Asn Asn Gly Ser Val Ile Arg Pro Val
 50                      55                  60

Lys Ala Met Tyr Thr Ser Ile Tyr Lys Leu Glu Glu Asn Ser Glu Glu
 65                  70                  75                  80

Asn Arg Leu Ser Lys Glu Arg Ser Phe Leu Leu Lys Asn Tyr Ser Ile
                 85                  90                  95

Lys Lys Glu Arg Phe Tyr Met Thr Thr Lys Asn Leu Ser Asp Leu Glu
                100                 105                 110

Met Glu Ile Ser Asn Asn Gln Gln Gln Leu Lys Arg Leu Ile Ala Pro
             115                 120                 125

Ala Phe Arg His Ile Val Leu Lys Val Pro Ala Ser Glu Glu Ser Asn
130                 135                 140

Tyr Lys Glu Ile Phe Gln Val Glu Pro Arg Tyr Ile Ala Gln Ala Leu
145                 150                 155                 160

Arg Leu Ala Asn Ala Phe Gln Gly Ala Leu Asp Pro Thr Asp Leu Asn
                165                 170                 175

Phe Asn Phe Glu Lys Ala Leu Gln Ile Ala Gln His Ile Pro Asn Ser
            180                 185                 190

Ala Ile Val Lys Thr Leu Asn Gln Asn Val Val Gln Gln Thr Val Glu
        195                 200                 205

Ile Ser Ala Met Ile Ser Gln Leu Lys Gln Ile Ile Lys Asp Val Leu
    210                 215                 220

Gly Leu Val Ile Ser Ser Pro Asn Phe Trp Asn Ser Val Glu Ala Ala
225                 230                 235                 240

Val Thr Asn Thr Phe Thr Asn Leu Ser Thr Gln Glu Asp Gly Ala Trp
                245                 250                 255

Ile Phe Trp Lys Ser Ser Ser Ser Asn Thr Ser Tyr Tyr Tyr Tyr Asn
            260                 265                 270

Ile Leu Phe Ser Ile Gln Asn Ala Glu Thr Gly Ala Val Met Ala Val
        275                 280                 285

Leu Pro Ile Ala Phe Glu Ile Ser Val Asn Leu Glu Lys Gln Lys Val
    290                 295                 300

Leu Phe Leu Thr Ile Arg Asp Ser Ala Arg Tyr Glu Val Lys Leu Lys
305                 310                 315                 320

Ala Ile Thr Leu Val Gln Ala Leu Asp Ser Phe Asn Ala Pro Ile Thr
                325                 330                 335

Asp Val Phe Asn Val His Asn Tyr Gly Pro Tyr Pro Pro Ile Asn Ser
            340                 345                 350

Asn Val Asn Asp Leu Ile Ile Arg Asn Leu Met Leu Asn Asn Thr Asn
        355                 360                 365

Ser Asn Asp Phe Ile Leu Gln Asp Leu Ile Asp Asn Gln His Asn Asp
    370                 375                 380

Lys Lys Glu
385

<210> SEQ ID NO 11
<211> LENGTH: 1200
<212> TYPE: DNA
<213> ORGANISM: Artificial Sequence
<220> FEATURE:
```

<223> OTHER INFORMATION: synthesized coding region

<400> SEQUENCE: 11

```
atgctgacct gcggaaggtt catcagctcc agcgcggcca ccagcaccgc ctccttcttc      60
ccgtttagga ccctgacaag gagcctggtg aggagaccgg ccccgcacct gctcagctcc     120
gcgtcagctg ccgccgccac agcggtggag ctggacacca acggagacgg ctcagcgggc     180
ggcggagccg cgtggtgag gcctcagtgg aaggcggcaa tcgacttcaa gtggatcagg      240
tacacctcca tctataagct ggaggagaac tccgaggaga cagactgtc caaggagagg      300
agcttcctgc tgaagaacta ctcaattaaa aaggagagat tctacatgac caccaagaac     360
ctgtccgacc tggagatgga gatcagcaat aatcaacagc agctgaagag gctgatcgca     420
ccggccttta ggcacatcgt attaaaggtg ccagccagcg aggagagcaa ctacaaggaa     480
atcttccaag tggagcctcg ctacatcgcc caagcgctga ggctggcgaa cgccttccaa     540
ggcgcactgg acccgaccga cctgaacttc aacttcgaga agcattgca gatcgctcag     600
cacatcccga cagcgccat cgtgaaaacc ctgaaccaaa cgtggtgca gcagaccgtg       660
gagatatccg ccatgatcag ccagctgaag cagatcatta agacgtgct gggcctggtg     720
atcagctccc gaacttctg gaactccgtg gaggctgccg tgaccaacac cttcaccaac      780
ctgtccaccc aagaggacgg agcgtggatc ttctggaagt ccagctcctc cagcaacacc    840
agctactact acaacatcct gttcagcatc cagaacgcgg agaccggagc cgtgatggcg    900
gtgctgccga ttgcgttcga gatttccgtg aacctggaga agcagaaggt gctgttcctg    960
accataaggg actccgcgag atacgaggtg aagctgaagg ctatcaccct ggtgcaagcg   1020
ctggactcct tcaacgcacc gatcaccgac gtgttcaacg tccacaacta cggtccgtac   1080
ccaccaataa acagcaacgt gaacgacctg atcatccgga acctgatgct gaacaacacc   1140
aactcaaacg acttcatcct ccaagacctg atcgacaatc aacacaacga caagaaggag   1200
```

<210> SEQ ID NO 12
<211> LENGTH: 400
<212> TYPE: PRT
<213> ORGANISM: Artificial Sequence
<220> FEATURE:
<223> OTHER INFORMATION: translated from synthesized coding region

<400> SEQUENCE: 12

```
Met Leu Thr Cys Gly Arg Phe Ile Ser Ser Ser Ala Ala Thr Ser Thr
1               5                   10                  15

Ala Ser Phe Phe Pro Phe Arg Thr Leu Thr Arg Ser Leu Val Arg Arg
            20                  25                  30

Pro Ala Pro His Leu Leu Ser Ser Ala Ser Ala Ala Ala Thr Ala
        35                  40                  45

Val Glu Leu Asp Thr Asn Gly Asp Gly Ser Ala Gly Gly Gly Ala Gly
    50                  55                  60

Val Val Arg Pro Gln Trp Lys Ala Ala Ile Asp Phe Lys Trp Ile Arg
65                  70                  75                  80

Tyr Thr Ser Ile Tyr Lys Leu Glu Glu Asn Ser Glu Glu Asn Arg Leu
                85                  90                  95

Ser Lys Glu Arg Ser Phe Leu Leu Lys Asn Tyr Ser Ile Lys Lys Glu
            100                 105                 110

Arg Phe Tyr Met Thr Thr Lys Asn Leu Ser Asp Leu Glu Met Glu Ile
        115                 120                 125

Ser Asn Asn Gln Gln Gln Leu Lys Arg Leu Ile Ala Pro Ala Phe Arg
```

```
                130               135              140
His Ile Val Leu Lys Val Pro Ala Ser Glu Ser Asn Tyr Lys Glu
145                 150              155                 160

Ile Phe Gln Val Glu Pro Arg Tyr Ile Ala Gln Ala Leu Arg Leu Ala
                165              170              175

Asn Ala Phe Gln Gly Ala Leu Asp Pro Thr Asp Leu Asn Phe Asn Phe
            180              185              190

Glu Lys Ala Leu Gln Ile Ala Gln His Ile Pro Asn Ser Ala Ile Val
            195              200              205

Lys Thr Leu Asn Gln Asn Val Val Gln Gln Thr Val Glu Ile Ser Ala
        210              215              220

Met Ile Ser Gln Leu Lys Gln Ile Ile Lys Asp Val Leu Gly Leu Val
225             230              235              240

Ile Ser Ser Pro Asn Phe Trp Asn Ser Val Glu Ala Ala Val Thr Asn
                245              250              255

Thr Phe Thr Asn Leu Ser Thr Gln Glu Asp Gly Ala Trp Ile Phe Trp
            260              265              270

Lys Ser Ser Ser Ser Asn Thr Ser Tyr Tyr Tyr Asn Ile Leu Phe
        275              280              285

Ser Ile Gln Asn Ala Glu Thr Gly Ala Val Met Ala Val Leu Pro Ile
290             295              300

Ala Phe Glu Ile Ser Val Asn Leu Glu Lys Gln Lys Val Leu Phe Leu
305             310              315              320

Thr Ile Arg Asp Ser Ala Arg Tyr Glu Val Lys Leu Lys Ala Ile Thr
                325              330              335

Leu Val Gln Ala Leu Asp Ser Phe Asn Ala Pro Ile Thr Asp Val Phe
            340              345              350

Asn Val His Asn Tyr Gly Pro Tyr Pro Pro Ile Asn Ser Asn Val Asn
            355              360              365

Asp Leu Ile Ile Arg Asn Leu Met Leu Asn Asn Thr Asn Ser Asn Asp
        370              375              380

Phe Ile Leu Gln Asp Leu Ile Asp Asn Gln His Asn Asp Lys Lys Glu
385             390              395              400

<210> SEQ ID NO 13
<211> LENGTH: 1032
<212> TYPE: DNA
<213> ORGANISM: Artificial Sequence
<220> FEATURE:
<223> OTHER INFORMATION: synthesized coding region

<400> SEQUENCE: 13
atggcgaaca agcacctgag cctgtccctg ttcctggtgc tgcttggcct gagcgcatcc      60
ctggcatccg gatacacctc catctataag ctggaggaga actccgagga gaacagactg     120
tccaaggaga ggagcttcct gctgaagcag tactcaatta aaaaggagag attctacatg     180
accaccaagc agctgtccga cctggagatg gagatcagca taatcaaca gcagctgaag      240 aggctgatcg caccggcctt taggcacatc gtattaaagg tgccagccag cgaggagagc     300
aactacaagg aaatcttcca agtggagcct cgctacatcg cccaagcgct gaggctggcg     360
aacgccttcc aaggcgcact ggacccgacc gacctgaact tcaacttcga gaaagcattg     420
cagatcgctc agcacatccc gaacagcgcc atcgtgaaaa ccctgaacca aaacgtggtg     480
cagcagaccg tggagatatc cgccatgatc agccagctga agcagatcat taagacgtg      540 ctgggcctgg tgatcagctc cccgaacttc tggaactccg tggaggctgc cgtgaccaac     600
```

```
accttcaccc agctgtccac ccaagaggac ggagcgtgga tcttctggaa gtccagctcc    660
tccagccaga ccagctacta ctacaacatc ctgttcagca tccagaacgc ggagaccgga    720
gccgtgatgg cggtgctgcc gattgcgttc gagatttccg tgaacctgga aagcagaag    780 gtgctgttcc tgaccataag ggactccgcg agatacgagg tgaagctgaa ggctatcacc    840
ctggtgcaag cgctggactc cttcaacgca ccgatcaccg acgtgttcaa cgtccacaac    900
tacggtccgt acccaccaat aaacagcaac gtgaacgacc tgatcatccg gaacctgatg    960
ctgcaaaaca ccaactcaaa cgacttcatc ctccaagacc tgatcgacaa tcaacacaac   1020
gacaagaagg ag                                                       1032
```

<210> SEQ ID NO 14
<211> LENGTH: 344
<212> TYPE: PRT
<213> ORGANISM: Artificial Sequence
<220> FEATURE:
<223> OTHER INFORMATION: translated from synthesized coding region

<400> SEQUENCE: 14

```
Met Ala Asn Lys His Leu Ser Leu Ser Leu Phe Leu Val Leu Leu Gly
1               5                   10                  15

Leu Ser Ala Ser Leu Ala Ser Gly Tyr Thr Ser Ile Tyr Lys Leu Glu
            20                  25                  30

Glu Asn Ser Glu Glu Asn Arg Leu Ser Lys Glu Arg Ser Phe Leu Leu
        35                  40                  45

Lys Gln Tyr Ser Ile Lys Lys Glu Arg Phe Tyr Met Thr Thr Lys Gln
    50                  55                  60

Leu Ser Asp Leu Glu Met Glu Ile Ser Asn Asn Gln Gln Gln Leu Lys
65                  70                  75                  80

Arg Leu Ile Ala Pro Ala Phe Arg His Ile Val Leu Lys Val Pro Ala
                85                  90                  95

Ser Glu Glu Ser Asn Tyr Lys Glu Ile Phe Gln Val Glu Pro Arg Tyr
            100                 105                 110

Ile Ala Gln Ala Leu Arg Leu Ala Asn Ala Phe Gln Gly Ala Leu Asp
        115                 120                 125

Pro Thr Asp Leu Asn Phe Asn Phe Glu Lys Ala Leu Gln Ile Ala Gln
    130                 135                 140

His Ile Pro Asn Ser Ala Ile Val Lys Thr Leu Asn Gln Asn Val Val
145                 150                 155                 160

Gln Gln Thr Val Glu Ile Ser Ala Met Ile Ser Gln Leu Lys Gln Ile
                165                 170                 175

Ile Lys Asp Val Leu Gly Leu Val Ile Ser Ser Pro Asn Phe Trp Asn
            180                 185                 190

Ser Val Glu Ala Ala Val Thr Asn Thr Phe Thr Gln Leu Ser Thr Gln
        195                 200                 205

Glu Asp Gly Ala Trp Ile Phe Trp Lys Ser Ser Ser Ser Gln Thr
    210                 215                 220

Ser Tyr Tyr Tyr Asn Ile Leu Phe Ser Ile Gln Asn Ala Glu Thr Gly
225                 230                 235                 240

Ala Val Met Ala Val Leu Pro Ile Ala Phe Glu Ile Ser Val Asn Leu
                245                 250                 255

Glu Lys Gln Lys Val Leu Phe Leu Thr Ile Arg Asp Ser Ala Arg Tyr
            260                 265                 270

Glu Val Lys Leu Lys Ala Ile Thr Leu Val Gln Ala Leu Asp Ser Phe
```

```
                275                 280                 285
Asn Ala Pro Ile Thr Asp Val Phe Asn Val His Asn Tyr Gly Pro Tyr
            290                 295                 300
Pro Pro Ile Asn Ser Asn Val Asn Asp Leu Ile Ile Arg Asn Leu Met
305                 310                 315                 320
Leu Gln Asn Thr Asn Ser Asn Asp Phe Ile Leu Gln Asp Leu Ile Asp
                325                 330                 335
Asn Gln His Asn Asp Lys Lys Glu
            340
```

<210> SEQ ID NO 15
<211> LENGTH: 1050
<212> TYPE: DNA
<213> ORGANISM: Artificial Sequence
<220> FEATURE:
<223> OTHER INFORMATION: synthesized coding region

<400> SEQUENCE: 15

```
atggcgaaca agcacctgag cctgtccctg ttcctggtgc tgcttggcct gagcgcatcc       60
ctggcatccg gatacacctc catctataag ctggaggaga actccgagga aacagactg      120
tccaaggaga ggagcttcct gctgaagcag tactcaatta aaaaggagag attctacatg     180
accaccaagc agctgtccga cctggagatg gagatcagca ataatcaaca gcagctgaag     240
aggctgatcg caccggcctt taggcacatc gtattaaagg tgccagccag cgaggagagc     300
aactacaagg aaatcttcca agtggagcct cgctacatcg cccaagcgct gaggctggcg     360
aacgccttcc aaggcgcact ggacccgacc gacctgaact tcaacttcga aaagcattg      420
cagatcgctc agcacatccc gaacagcgcc atcgtgaaaa ccctgaacca aaacgtggtg     480
cagcagaccg tggagatatc cgccatgatc agccagctga gcagatcat  taagacgtg      540
ctgggcctgg tgatcagctc ccgaacttc tggaactccg tggaggctgc cgtgaccaac      600
accttcaccc agctgtccac ccaagaggac ggagcgtgga tcttctggaa gtccagctcc     660
tccagccaga ccagctacta ctacaacatc ctgttcagca tccagaacgc ggagaccgga     720
gccgtgatgg cggtgctgcc gattgcgttc gagatttccg tgaacctgga aagcagaag      780
gtgctgttcc tgaccataag ggactccgcg agatacgagg tgaagctgaa ggctatcacc     840
ctggtgcaag cgctggactc cttcaacgca ccgatcaccg acgtgttcaa cgtccacaac     900
tacggtccgt acccaccaat aaacagcaac gtgaacgacc tgatcatccg gaacctgatg     960
ctgcaaaaca ccaactcaaa cgacttcatc ctccaagacc tgatcgacaa tcaacacaac    1020
gacaagaagg agagcgagaa ggacgagctg                                     1050
```

<210> SEQ ID NO 16
<211> LENGTH: 350
<212> TYPE: PRT
<213> ORGANISM: Artificial Sequence
<220> FEATURE:
<223> OTHER INFORMATION: translated from synthesized coding region

<400> SEQUENCE: 16

```
Met Ala Asn Lys His Leu Ser Leu Ser Leu Phe Leu Val Leu Leu Gly
1               5                   10                  15
Leu Ser Ala Ser Leu Ala Ser Gly Tyr Thr Ser Ile Tyr Lys Leu Glu
            20                  25                  30
Glu Asn Ser Glu Glu Asn Arg Leu Ser Lys Glu Arg Ser Phe Leu Leu
        35                  40                  45
```

```
Lys Gln Tyr Ser Ile Lys Lys Glu Arg Phe Tyr Met Thr Thr Lys Gln
 50              55                  60

Leu Ser Asp Leu Glu Met Glu Ile Ser Asn Asn Gln Gln Gln Leu Lys
 65              70                  75                      80

Arg Leu Ile Ala Pro Ala Phe Arg His Ile Val Leu Lys Val Pro Ala
                 85                  90                  95

Ser Glu Glu Ser Asn Tyr Lys Glu Ile Phe Gln Val Glu Pro Arg Tyr
                100                 105                 110

Ile Ala Gln Ala Leu Arg Leu Ala Asn Ala Phe Gln Gly Ala Leu Asp
            115                 120                 125

Pro Thr Asp Leu Asn Phe Asn Phe Glu Lys Ala Leu Gln Ile Ala Gln
            130                 135                 140

His Ile Pro Asn Ser Ala Ile Val Lys Thr Leu Asn Gln Asn Val Val
145                 150                 155                 160

Gln Gln Thr Val Glu Ile Ser Ala Met Ile Ser Gln Leu Lys Gln Ile
                165                 170                 175

Ile Lys Asp Val Leu Gly Leu Val Ile Ser Ser Pro Asn Phe Trp Asn
                180                 185                 190

Ser Val Glu Ala Ala Val Thr Asn Thr Phe Thr Gln Leu Ser Thr Gln
            195                 200                 205

Glu Asp Gly Ala Trp Ile Phe Trp Lys Ser Ser Ser Ser Gln Thr
            210                 215                 220

Ser Tyr Tyr Tyr Asn Ile Leu Phe Ser Ile Gln Asn Ala Glu Thr Gly
225                 230                 235                 240

Ala Val Met Ala Val Leu Pro Ile Ala Phe Glu Ile Ser Val Asn Leu
                245                 250                 255

Glu Lys Gln Lys Val Leu Phe Leu Thr Ile Arg Asp Ser Ala Arg Tyr
                260                 265                 270

Glu Val Lys Leu Lys Ala Ile Thr Leu Val Gln Ala Leu Asp Ser Phe
            275                 280                 285

Asn Ala Pro Ile Thr Asp Val Phe Asn Val His Asn Tyr Gly Pro Tyr
            290                 295                 300

Pro Pro Ile Asn Ser Asn Val Asn Asp Leu Ile Ile Arg Asn Leu Met
305                 310                 315                 320

Leu Gln Asn Thr Asn Ser Asn Asp Phe Ile Leu Gln Asp Leu Ile Asp
                325                 330                 335

Asn Gln His Asn Asp Lys Lys Glu Ser Glu Lys Asp Glu Leu
                340                 345                 350
```